United States Patent
Intlekofer et al.

(10) Patent No.: US 11,788,112 B2
(45) Date of Patent: Oct. 17, 2023

(54) L-2-HYDROXYGLUTARATE AND STRESS INDUCED METABOLISM

(71) Applicant: Memorial Sloan-Kettering Cancer Center, New York, NY (US)

(72) Inventors: Andrew M. Intlekofer, New York, NY (US); Craig B. Thompson, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 603 days.

(21) Appl. No.: 16/452,297

(22) Filed: Jun. 25, 2019

(65) Prior Publication Data

US 2020/0032315 A1 Jan. 30, 2020

Related U.S. Application Data

(62) Division of application No. 15/129,167, filed as application No. PCT/US2015/023038 on Mar. 27, 2015, now Pat. No. 10,450,596.

(60) Provisional application No. 61/972,091, filed on Mar. 28, 2014.

(51) Int. Cl.
| | |
|---|---|
| *C12Q 1/32* | (2006.01) |
| *A61K 31/711* | (2006.01) |
| *G01N 33/50* | (2006.01) |

(52) U.S. Cl.
CPC .............. *C12Q 1/32* (2013.01); *A61K 31/711* (2013.01); *G01N 33/5091* (2013.01); *G01N 2500/10* (2013.01); *G01N 2800/7038* (2013.01)

(58) Field of Classification Search
None
See application file for complete search history.

(56) References Cited

U.S. PATENT DOCUMENTS

| | | |
|---|---|---|
| 10,450,596 B2 | 10/2019 | Intlekofer et al. |
| 11,262,362 B2 | 3/2022 | Wise et al. |
| 2002/0192737 A1 | 12/2002 | Kaelin et al. |

(Continued)

FOREIGN PATENT DOCUMENTS

| | | |
|---|---|---|
| JP | 2013-506833 A | 2/2013 |
| WO | WO-2004/046729 A2 | 6/2004 |

(Continued)

OTHER PUBLICATIONS

Chen et al., J. Inher. Metab. Dis. 19: 335-343 (1996).*

(Continued)

*Primary Examiner* — Erin M. Bowers
(74) *Attorney, Agent, or Firm* — Wolf, Greenfield & Sacks, P.C.

(57) ABSTRACT

The present disclosure provides, among other things, methods and compositions for diagnosing and treating stress-induced injuries, hypoxia in particular. The present invention is based, in part, on the novel discovery that a metabolite, L-2-hydroxyglutarate, and certain enzymes and substrates regulating its metabolism, mediate stress-induced cellular mechanisms. In some embodiments, provided methods and compositions are used to diagnose and treat diseases with hypoxia-induced injuries. In some embodiments, provided methods and compositions are used to modulate cell pluripotency or differentiation in vivo or in vitro.

9 Claims, 7 Drawing Sheets

Specification includes a Sequence Listing.

(56) References Cited

U.S. PATENT DOCUMENTS

| | | | |
|---|---|---|---|
| 2006/0084123 | A1 | 4/2006 | Harris et al. |
| 2009/0186358 | A1 | 7/2009 | Melville et al. |
| 2012/0202883 | A1 | 8/2012 | Hai et al. |
| 2013/0109643 | A1 | 5/2013 | Riggins et al. |
| 2013/0316385 | A1 | 11/2013 | Cantley et al. |
| 2014/0067234 | A1 | 3/2014 | Brown |
| 2014/0314728 | A1 | 10/2014 | Wise et al. |
| 2016/0033533 | A1 | 2/2016 | Wise et al. |
| 2017/0175164 | A1 | 6/2017 | Intlekofer et al. |

FOREIGN PATENT DOCUMENTS

| | | |
|---|---|---|
| WO | WO-2010/105243 A1 | 9/2010 |
| WO | WO-2011/040874 A1 | 4/2011 |
| WO | WO-2011/050211 A2 | 4/2011 |
| WO | WO-2011/143160 A2 | 11/2011 |
| WO | WO-2013/075065 A1 | 5/2013 |
| WO | WO-2013/086365 A2 | 6/2013 |

OTHER PUBLICATIONS

Steinhorn, Clin. Ped. Emerg. Med. 9: 169-175 (2008).*

Achouri, Y. et al., Identification of a dehydrogenase acting on D-2-hydroxyglutarate, The Biochemical Journal 381, 35-42 (2004).

Albers, E., et al., Distribution of 14C-labelled carbon from glucose and glutamate during anaerobic growth of *Saccharomyces cerevisiae*, Microbiology 144 ( Pt 6), 1683-1690 (1998).

Amary, M.F., et al., IDH1 and IDH2 mutations are frequent events in central chondrosarcoma and central and periosteal chondromas but not in other mesenchymal tumours, The Journal of Pathology 224, 334-343 (2011).

Author Not Known, Definition of Chronic Hypoxia, Mosby's Dictionary of Medicine, Nursing, and Health Professions, 9th Edition (Print), p. 363 (2012).

Banks, J.L., et al., Integrated Modeling Program, Applied Chemical Theory (IMPACT), Journal of Computational Chemistry 26, 1752-1780 (2005).

Bensaad, K., and Harris, A.L., Hypoxia and metabolism in cancer, Advances in Experimental Medicine and Biology 772, 1-39 (2014).

Bethesda Hyperbaric Oxygen Therapy, Epilepsy—Bethesda Hyperbaric Oxygen Therapy, 3 pages, (2009), <https://www.bethesdahbot.com/other-uses-of-hbot/epilespy/>. Retrieved Feb. 1, 2018.

Borger, D.R., et al., Frequent mutation of isocitrate dehydrogenase (IDH)1 and IDH2 in cholangiocarcinoma identified through broad-based tumor genotyping, The Oncologist 17, 72-79 (2012).

Bristow, R. G. and Hill, R. P., Hypoxia, DNA repair and genetic instability, Nature Reviews, 8: 180-192 (2008).

Brown, J. M., Chapter 15: Tumor Hypoxia in Cancer Therapy, Methods in Enzymology, Section 4: Hypoxia and Tumor Biology, 35:295-321 (2007).

Cairns, R.A., et al., IDH2 mutations are frequent in angioimmunoblastic T-cell lymphoma, Blood, 119:1901-1903 (2012).

Chang, C. M. et al., The Role of Isocitrate Dehydrogenase Mutations in Glioma Brain Tumors, Molecular Targets ofCNS Tumors, pp. 413-436 (2011).

Chen, C., et al., Cancer-associated IDH2 mutants drive an acute myeloid leukemia that is susceptible to Brd4 inhibition, Genes & Development, 27:1974-1985 (2013).

Chowdhury, R., et al., The oncometabolite 2-hydroxyglutarate inhibits histone lysine demethylases, EMBO Reports, 12:463-469 (2011).

Dang, L.et al., Cancer-associated IDH1 mutations produce 2-hydroxyglutarate, Nature, 462(7274):739-44 (2009).

Deberardinis, R.J. et al., Beyond aerobic glycolysis: transformed cells can engage in glutamine metabolism that exceeds the requirement for protein and nucleotide synthesis, Proc. Natl. Acad. Sci. USA, 104(49):19345-50 (2007).

Duan, J.X. et al., Potent and highly selective hypoxia-activated achiral phosphoramidate mustards as anticancer drugs, J. Med. Chem., 51(8):2412-20 (2008).

Extended European Search Report for EP 12850119.4, 13 pages (dated Sep. 2, 2015).

Figueroa, M.E. et al., Leukemic IDH1 and IDH2 mutations result in a hypermethylation phenotype, disrupt TET2 function, and impair hematopoietic differentiation, Cancer Cell, 18:553-567 (2010).

Friesner, R.A., et al., Extra precision glide: docking and scoring incorporating a model of hydrophobic enclosure for protein-ligand complexes, Journal of Medicinal Chemistry, 49:6177-6196 (2006).

Friesner, R.A., et al., Glide: a new approach for rapid, accurate docking and scoring. 1. Method and assessment of docking accuracy, Journal of Medicinal Chemistry, 47:1739-1749 (2004).

Gross, S., et al., Cancer-associated metabolite 2-hydroxyglutarate accumulates in acute myelogenous leukemia with isocitrate dehydrogenase 1 and 2 mutations, The Journal of Experimental Medicine, 207:339-344 (2010).

Haacke, M. E. et al, Observing tumor vascularity noninvasively using magnetic resonance imaging, Image Anal Stereol, 21:107-113 (2002).

Halgren, T.A., et al., Glide: a new approach for rapid, accurate docking and scoring. 2. Enrichment factors in database screening, Journal of Medicinal Chemistry, 47:1750-1759 (2004).

Haliloglu, G., et al., L-2-hydroxyglutaric aciduria and brain tumors in children with mutations in the L2HGDH gene: neuroimaging findings, Neuropediatrics, 39:119-122 (2008).

Hu, C.J., et al., Differential roles of hypoxia-inducible factor 1 alpha (HIF-1alpha) and HIF-2alpha in hypoxic gene regulation, Molecular and Cellular Biology, 23:9361-9374 (2003).

International Search Report for PCT/US2012/065731, 2 pages (dated Feb. 8, 2013).

International Search Report for PCT/US2015/23038, 5 pages (dated Aug. 19, 2015).

Jacobson, M.P., et al., A hierarchical approach to all-atom protein loop prediction, Proteins, 55:351-367 (2004).

Jacobson, M.P., et al., On the role of the crystal environment in determining protein side-chain conformations, Journal of Molecular Biology, 320:597-608 (2002).

Kaelin, W.G., Jr., and McKnight, S.L., Influence of metabolism on epigenetics and disease, Cell, 153:56-69 (2013).

Kaelin, W.G., Jr., and Ratcliffe, P.J., Oxygen sensing by metazoans: the central role of the HIF hydroxylase pathway, Molecular Cell, 30:393-402 (2008).

Kats, L.M., et al., Proto-oncogenic role of mutant IDH2 in leukemia initiation and maintenance, Cell Stem Cell, 14:329-341 (2014).

Kaur, B. et al, Hypoxia and the hypoxia-inducible-factor pathway in glioma growth and angiogenesis, Neuro. Oncol., 7(2): 134-53 (2005).

Kim, J.W. et al., HIF-1-mediated expression of pyruvate dehydrogenase kinase: a metabolic switch required for cellular adaptation to hypoxia, Cell Metab., 3(3):177-85 (2006).

Kohshi, K. et al, Radiotherapy after hyperbaric oxygenation for malignant gliomas: a pilot study, J. Cancer Res. Clin. Oncol., 122: 676-678 (1996).

Koivunen, P., et al., Transformation by the (R)-enantiomer of 2-hydroxyglutarate linked to EGLN activation, Nature, 483:484-488 (2012).

Kooistra, S.M., and Helin, K., Molecular mechanisms and potential functions of histone demethylases. Nature Reviews Molecular Cell Biology, 13:297-311 (2012).

Kranendijk, M., et al., Progress in understanding 2-hydroxyglutaric acidurias, Journal of Inherited Metabolic Disease, 35(4):571-587 (2012).

Ley, T.J., et al., DNA sequencing of a cytogenetically normal acute myeloid leukaemia genome, Nature, 456:66-72 (2008).

Linster, C.L., et al., Metabolite damage and its repair or pre-emption, Nature Chemical Biology, 9:72-80 (2013).

Losman, J.A., and Kaelin, W.G., Jr., What a difference a hydroxyl makes: mutant IDH, (R)-2-hydroxyglutarate, and cancer, Genes & Development, 27:836-852 (2013).

Losman, J.A., et al., (R)-2-hydroxyglutarate is sufficient to promote leukemogenesis and its effects are reversible, Science, 339:1621-1625 (2013).

Lu, C., et al., IDH mutation impairs histone demethylation and results in a block to cell differentiation, Nature, 483:474-478 (2012).

(56) References Cited

OTHER PUBLICATIONS

Lum, J.J. et al., The transcription factor HIF-1alpha plays a critical role in the growth factor-dependent regulation of both aerobic and anaerobic glycolysis, Genes Dev., 21(9):1037-49 (2007).
Meister, A., Reduction of alpha gamma-diketo and alpha-keto acids catalyzed by muscle preparations and by crystalline lactic dehydrogenase, The Journal of Biological Chemistry, 184:117-129 (1950).
Metallo, C.M., et al., Reductive glutamine metabolism by IDH1 mediates lipogenesis under hypoxia, Nature, 481:380-384 (2012).
Metellus, P. et al., IDH mutation status impact on in vivo hypoxia biomarkers expression: new insights from a clinical, nuclear imaging and immunohistochemical study in 33 glioma patients, J. Neurooncol., 105(3):591-600 (2011).
Millard, P., et al., IsoCor: correcting MS data in isotope labeling experiments, Bioinformatics, 28:1294-1296 (2012).
Moroni, I., et al., L-2-hydroxyglutaric aciduria and brain malignant tumors: a predisposing condition? Neurology, 62:1882-1884 (2004).
Nombela-Arrieta, C., et al., Quantitative imaging of haematopoietic stem and progenitor cell localization and hypoxic status in the bone marrow microenvironment, Nature Cell Biology, 15:533-543 (2013).
Olsson, M.H.M., et al., PROPKA3: Consistent Treatment of Internal and Surface Residues in Empirical pK(a) Predictions, J Chem Theory Comput, 7:525-537 (2011).
Ozer, A., and Bruick, R.K., Non-heme dioxygenases: cellular sensors and regulators jelly rolled into one? Nature Chemical Biology, 3:144-153 (2007).
Papandreou, I. et al., HIF-1 mediates adaptation to hypoxia by actively downregulating mitochondrial oxygen consumption, Cell Metab., 3(3):187-97 (2006).
Parsons, D.W., et al., An integrated genomic analysis of human glioblastoma multiforme, Science, 321:1807-1812 (2008).
Partial Supplementary European Search Report for 12850119.4, 5 pages (dated Apr. 21, 2015).
Patel, J.P., et al., Prognostic relevance of integrated genetic profiling in acute myeloid leukemia, The New England Journal of Medicine, 366:1079-1089 (2012).
Patiar, S. and Harris, A.L., Role of hypoxia-inducible factor-1 alpha as a cancer therapy target, Endocr. Relat. Cancer, 13 Suppl 1:S61-75 (2006).
Patterson, A.L., et al., Absolute Configuration of Naturally Occurring Isocitric Acid, J Am Chem Soc, 84:309-310 (1962).
Rakheja, D. et al., Papillary thyroid carcinoma shows elevated levels of 2-hydroxyglutarate, Tumor Biology, 32:325-333 (2011).
Read, J.A., et al., Structural basis for altered activity of M- and H-isozyme forms of human lactate dehydrogenase, Proteins, 43:175-185 (2001).
Rohle, D., et al., An inhibitor of mutant IDH1 delays growth and promotes differentiation of glioma cells, Science, 340:626-630 (2013).
Rzem, R., et al., A gene encoding a putative FAD-dependent L-2-hydroxyglutarate dehydrogenase is mutated in L-2-hydroxyglutaric aciduria, Proceedings of the National Academy of Sciences of the United States of America, 101:16849-16854 (2004).
Rzem, R., et al., L-2-hydroxyglutaric aciduria, a defect of metabolite repair, Journal of Inherited Metabolic Disease, 30:681-689 (2007).
Sasaki, M., et al., IDH1(R132H) mutation increases murine haematopoietic progenitors and alters epigenetics, Nature, 488:656-659 (2012).
Schaap, F. et al., Mutations in the Isocitrate Dehydrogenase Genes IDH1 and IDH2 in Tumors, Adv Anat. Pathol., 20:32-38 (2013).
Schatz, L., and Segal, H.L., Reduction of alpha-ketoglutarate by homogeneous lactic dehydrogenase X of testicular tissue, The Journal of biological chemistry, 244:4393-4397 (1969).
Seijo-Martinez, M. et al, L-2-Hydroxyglutaric Aciduria, Arch Neurol., 62: 666-670 (2005).
Semenza, G.L., HIF-1 mediates metabolic responses to intratumoral hypoxia and oncogenic mutations, The Journal of Clinical Investigation, 123: 3664-3671 (2013).

Shim, E.H., et al., L-2-Hydroxyglutarate: An Epigenetic Modifier and Putative Oncometabolite in Renal Cancer, Cancer Discovery, 4:1290-1298 (2014).
Simon, M.C., and Keith, B., The role of oxygen availability in embryonic development and stem cell function, Nature Reviews Molecular Cell Biology, 9:285-296 (2008).
Sondergaard, C.R., et al., Improved Treatment of Ligands and Coupling Effects in Empirical Calculation and Rationalization of pK(a) Values, J Chem Theory Comput, 7:2284-2295 (2011).
Spencer, J.A., et al., Direct measurement of local oxygen concentration in the bone marrow of live animals, Nature, 508:269-273 (2014).
Sprecher, M., et al., Stereochemical Course of the Isocitrate Lyase Reaction, The Journal of Biological Chemistry, 239:4268-4271 (1964).
Steenweg, M. E. et al, L-2-Hydroxyglutaric Aciduria: PAttern of MR Imaging Abnormalities in 56 Patients, Radiology, 251(3): 856-865 (2009).
Struys, E.A. et al., Measurement of urinary D- and L-2-hydroxyglutarate enantiomers by stable-isotope-dilution liquid chromatography-tandem mass spectrometry after derivatization with diacetyl-L-tartaric anhydride, Clin. Chem., 50(8):1391-5 (2004).
Struys, E.A., et al., Mutations in the D-2-hydroxyglutarate dehydrogenase gene cause D-2-hydroxyglutaric aciduria, American Journal of Human Genetics, 76:358-360 (2005).
Struys, E.A., et al., Novel insights into L-2-hydroxyglutaric aciduria: mass isotopomer studies reveal 2-oxoglutaric acid as the metabolic precursor of L-2-hydroxyglutaric acid, Journal of Inherited Metabolic Disease, 30:690-693 (2007).
Suda, T., et al., Metabolic regulation of hematopoietic stem cells in the hypoxic niche, Cell Stem Cell, 9:298-310 (2011).
Tausendschon, M., et al., Hypoxia causes epigenetic gene regulation in macrophages by attenuating Jumonji histone demethylase activity, Cytokine, 53:256-262 (2011).
Terunuma, A., et al., MYC-driven accumulation of 2-hydroxyglutarate is associated with breast cancer prognosis, The Journal of Clinical Investigation, 124:398-412 (2014).
Vander Heiden, M.G., et al., Understanding the Warburg effect: the metabolic requirements of cell proliferation, Science, 324:1029-1033 (2009).
Venneti, S., et al., Evaluation of histone 3 lysine 27 trimethylation (H3K27me3) and enhancer of Zest 2 (EZH2) in pediatric glial and glioneuronal tumors shows decreased H3K27me3 in H3F3A K27M mutant glioblastomas, Brain Pathol, 23:558-564 (2013).
Venneti, S., et al., Histone 3 lysine 9 trimethylation is differentially associated with isocitrate dehydrogenase mutations in oligodendrogliomas and high-grade astrocytomas, Journal of Neuropathology and Experimental Neurology, 72:298-306 (2013).
Wang, F., et al., Targeted inhibition of mutant IDH2 in leukemia cells induces cellular differentiation, Science, 340:622-626 (2013).
Wang, Y.H., et al., Cell-state-specific metabolic dependency in hematopoiesis and leukemogenesis, Cell, 158:1309-1323 (2014).
Ward, P.S. et al., Identification of additional IDH mutations associated with oncometabolite R(−)-2-hydroxyglutarate production, Oncogene, 31(19):2491-8 (2012).
Ward, P.S. et al., The common feature of leukemia-associated IDH1 and IDH2 mutations is a neomorphic enzyme activity converting alpha-ketoglutarate to 2-hydroxyglutarate, Cancer Cell, 17(3):225-34 (2010).
Ward, P.S., and Thompson, C.B., Metabolic reprogramming: a cancer hallmark even warburg did not anticipate, Cancer Cell, 21:297-308 (2012).
Wise, D.R. et al., Hypoxia promotes isocitrate dehydrogenase-dependent carboxylation of a-ketoglutarate to citrate to support cell growth and viability, Proc. Natl. Acad. Sci. U S A., 108(49):19611-6 (2011).
Wise, D.R. et al., Myc regulates a transcriptional program that stimulates mitochondrial glutaminolysis and leads to glutamine addiction, Proc. Natl. Acad. Sci. USA, 105(48):18782-7 (2008).
Wise, D.R., and Thompson, C.B., Glutamine addiction: a new therapeutic target in cancer, Trends in Biochemical Sciences, 35:427-433 (2010).

(56) References Cited

OTHER PUBLICATIONS

Written Opinion for PCT/US2012/065731, 7 pages (dated Feb. 8, 2013).
Written Opinion for PCT/US2015/23038, 11 pages (dated Aug. 19, 2015).
Xie, H., et al., Targeting lactate dehydrogenase—a inhibits tumorigenesis and tumor progression in mouse models of lung cancer and impacts tumor-initiating cells, Cell Metabolism, 19:795-809 (2014).
Xu, W., et al., Oncometabolite 2-hydroxyglutarate is a competitive inhibitor of alpha-ketoglutarate-dependent dioxygenases, Cancer Cell, 19:17-30 (2011).
Yan, H., et al., IDH1 and IDH2 mutations in gliomas, The New England Journal of Medicine, 360:765-773 (2009).
Zhdanov, A.V., et al., Differential contribution of certain metabolic substrates and cellular oxygen in HIF signalling, Experimental Cell Research (2014).
PCT/US2012/065731, May 30, 2014, International Preliminary Report on Patentability.
EP 15768552.0, Aug. 14, 2017, Partial Supplementary European Search Report.
EP 15768552.0, Nov. 14, 2017, Extended European Search Report.
PCT/US2015/023038, Jun. 25, 2015, Invitation to Pay Additional Fees.
PCT/US2015/023038, Oct. 4, 2016, International Preliminary Report on Patentability.
International Preliminary Report on Patentability dated May 30, 2014 for International Application No. PCT/US2012/065731.
Partial Supplementary European Search Report dated Aug. 14, 2017 for European Application No. 15768552.0.
Extended European Search Report dated Nov. 14, 2017 for European Application No. 15768552.0.
Invitation to Pay Additional Fees dated Jun. 25, 2015 for International Application No. PCT/US2015/023038.
International Preliminary Report on Patentability dated Oct. 4, 2016 for International Application No. PCT/US2015/023038.
Delaney et al. How Can Hyperbaric Oxygen Contribute to Treatment? Phys Sportsmed. Mar. 2001;29(3):77-84. doi: 10.3810/psm.2001.03.681.
Intlekofer et al. Hypoxia Induces Production of L-2-Hydroxyglutarate. Cell Metab. Aug. 4, 2015;22(2):304-11. doi: 10.1016/j.cmet.2015.06.023. Epub Jul. 23, 2015.
SYTSMA. The Basics of Experimental Design [A Quick and Non-Technical Guide] 2009 pp. 1-11.

* cited by examiner

L-2-HYDROXYGLUTARATE AND STRESS INDUCED METABOLISM

RELATED APPLICATIONS

This application is a divisional of U.S. application Ser. No. 15/129,167, filed on Sep. 26, 2016, which is a 35 U.S.C. § 371 National Stage Entry of International Application No. PCT/US2015/023038, filed Mar. 27, 2015, which designates the U.S., and which claims the benefit of and priority to U.S. Provisional Patent Application Ser. No. 61/972,091, filed Mar. 28, 2014, the content of each of which is hereby incorporated by reference in its entirety for any and all purposes.

GOVERNMENT SUPPORT

This invention was made with government support under grant number CA168802 awarded by the National Institutes of Health. The government has certain rights in the invention.

SEQUENCE LISTING

In accordance with 37 CFR 1.52(e)(5), a Sequence Listing in the form of a text file (entitled "2016-12-14 Sequence Listing", created on Dec. 14, 2016, and having a size of 3,496 bytes) is incorporated herein by reference in its entirety.

BACKGROUND

Stress, such as hypoxia, infection, starvation, temperature, toxicity and the like significantly affects metabolism of the cells and contributes to major diseases. For example, most cells require oxygen to live and carry out their functions, and hypoxia affects cellular metabolic pathways, often causing hypoxia-induced injuries. New developments in cell response to stress research will lead to better treatments for disorders involving stress-induced injuries. There is a great deal of effort aimed at developing compositions or systems for treating diseases related to stress.

SUMMARY

The present disclosure encompasses the recognition that L-2HG plays an important role in tissue hypoxia. The present disclosure demonstrates that, among other applications, L-2HG can be used as a biomarker for diagnosing tissue hypoxia. In some embodiments, the present disclosure describes systems for diagnosing tissue hypoxia, for example by measuring cellular L-2HG from a sample taken from a subject. In some embodiments, the present disclosure describes that levels of L-2HG from a subject can be compared to those from a normoxia control subject. In some embodiments, the present disclosure describes that levels of L-2HG from a subject can be compared to those from a patient with acute hypoxia or chronic hypoxia. In some embodiments, the present disclosure describes that comparison of L-2HG from these different samples could be used to diagnose hypoxia in a subject. In some embodiments, the present disclosure describes that hypoxia status of a sample could be ascertained by measuring L-2HG levels.

Alternatively or additionally, the present disclosure describes diagnosing hypoxia-induced injury in a patient. Hypoxia-induced injuries that are not symptomatic or sub-symptomatic are often difficult to clinically diagnose. Measuring L-2HG levels from a sample in accordance with the present disclosure could give indication for hypoxia-induced injury in a subject. In some embodiments, the present disclosure describes systems for diagnosing tissue hypoxia by measuring cellular L-2HG, for example from a sample taken from a subject. In some embodiments, a sample could be, for example, a blood sample or a biopsy sample. In some embodiments, the present disclosure describes that levels of L-2HG from a subject can be compared to those from a normoxia control subject. In some embodiments, the present disclosure describes that levels of L-2HG from a subject can be compared to those from a patient with acute hypoxia or chronic hypoxia. In some embodiments, the present disclosure describes the comparison of L-2HG from these different samples could be used to diagnose hypoxia-induced injury in a subject.

The present disclosure describes that L-2HG could be used as a single metabolite for diagnosing hypoxia or hypoxia-induced injury. Alternatively or additionally, the present disclosure alternatively or additionally describes methods by which L-2HG can be integrated into a broader set of biomarkers for diagnosis. In some embodiments, the present disclosure describes methods that use L-2HG as part of a biomarker set in diagnosis. For example, in some embodiments, the present disclosure describes method that measure at least two biomarkers in a sample from the subject, wherein one of the at least two biomarkers is L-2HG.

The present disclosure describes that L-2HG is a novel and reliable factor for hypoxia-related diagnosis and therapy. Alternatively or additionally, in some embodiments, the present disclosure describes mechanisms by which certain enzymes that regulate L-2HG metabolism, for example, LDHA, MDH1, MDH2, and L-2-hydroxyglutarate dehydrogenase regulate L-2HG. In some embodiments, the present disclosure demonstrates that modulating of these enzymes could affect L-2HG levels in a predictable manner. In some embodiments, the present disclosure describes systems for modulating these enzymes for hypoxia-related diagnosis and therapy.

In some embodiments, the present disclosure describes diagnosis of hypoxia according to measurement of oxygen levels in a sample. In some embodiments, the present disclosure describes that hypoxia can be diagnosed via other methods. In some embodiments, the present disclosure describes the use of L-2HG in chronic hypoxia. In some embodiments, the present disclosure describes the use of L-2HG in acute hypoxia. In some embodiments, the present disclosure describes the use of L-2HG in hypoxia caused by the underlying cause of hypoxia, either chronic or acute.

In some embodiments, in accordance with the present invention, one or more hypoxia markers as described herein is detected or measured, for example, in a context of diagnosing or treating hypoxia or a hypoxia-related disease, disorder, or condition.

In some embodiments, a hypoxia-related disease, disorder or condition is or comprises, for example, septic shock, ischemic stroke, myocardial infarction, anemia, pulmonary disease, airway obstruction, acute respiratory distress syndrome, pneumonia, pneumothorax, emphysema, congenital heart defects, atherosclerosis, thrombosis, pulmonary embolism, pulmonary edema, asthma, cystic fibrosis, cancer, as well as during surgical procedures.

The present disclosure describes systems for identifying or characterizing agents useful in the treatment of hypoxia or hypoxia-induced injury. In some embodiments, the present disclosure describes certain novel parameters may play important roles in hypoxia. For example, in some embodiments, this parameter is or comprises of level or kinetics of L-2HG. In some embodiments, this parameter is or comprises of level or kinetics of alpha-ketoglutarate. In some embodiments, this parameter is or comprises of level or activity of LDHA. In some embodiments, this parameter is or comprises of level or activity of LDHA. In some embodiments, this parameter is or comprises of level or activity of MDH1. In some embodiments, this parameter is or comprises of level or activity of MDH2. In some embodiments, this parameter is or comprises of level or activity of L-2-hydroxyglutarate dehydrogenase.

In some embodiments, the present disclosure describes systems for identifying or characterizing agents useful in the treatment of hypoxia or hypoxia-induced injury by using L-2HG. For example, level of L-2HG in a cell, a tissue or an organism can be measured when the agent is present as compared with when it is absent or when a reference agent is present whose effect on L-2HG level in the tissue or organism is known. In some embodiments, an agent is identified or characterized as useful in the treatment of hypoxia-induced injury if the measured L-2HG level when the agent is present is higher than that when it is absent, is similar to that measured when a reference agent known to increase L-2HG is present, or is greater than that measured when a reference agent known not to increase L-2HG is present.

The present disclosure describes parameters against which L-2HG levels can be compared, for example, with diagnosing or treating hypoxia or hypoxia-induced injury. To give but one example, in some embodiments, the present disclosure describes treatment of hypoxia by administration of a hypoxia therapy to a subject whose L-2HG level is elevated compared to that of a normoxic reference subject. In some embodiments, an elevated level of L-2HG is at least two-fold, at least three-fold, at least four-fold, at least five-fold, at least six-fold, at least seven-fold, at least eight-fold, at least nine-fold, at least ten-fold, or even higher as compared with that observed for a normoxic subject.

In some embodiments, the present disclosure provides technologies for stratifying patient populations (e.g., with respect to their candidacy for treatment with hypoxia therapy), or for monitoring effectiveness of or modulating particular therapy as administered to one or more subjects.

In some embodiments, a hypoxia therapy may be or include, for example, supplemental oxygen therapy, transfusion of packed red blood cells, caffeine, vitamin therapy, mechanical ventilation, positive pressure therapy, physical exercise, or surgical intervention.

In some embodiments, a hypoxia marker as described herein is measured in a patient sample. In some embodiments a sample may be or comprise a tissue sample, for example from a heart, artery, brain, tumor, or combinations thereof. In some embodiments, a sample may be or comprise blood, urine, serum, lymph or cerebrospinal fluid. In some embodiments, a sample may be or comprise a venous blood sample.

In some embodiments, the present disclosure describes novel systems for treating hypoxia or hypoxia-induced injuries. In some embodiments, the injury is or comprises a symptom from a patient with a hypoxia-related disease, disorder or condition. In some embodiments, the injury is or comprises ischemic tissue injury.

In some embodiments, the present disclosure describes therapies that modulate L-2HG levels in a tissue or systematically. In some embodiments, the present disclosure describes therapies that increase the level of L-2HG in the subject. In some embodiments, the present disclosure describes therapies that decrease the level of L-2HG in the subject.

In some embodiments, the present disclosure describes therapies that include administration of a composition comprising an agent that modulate L-2HG metabolism. In some embodiments, the present disclosure describes therapies that include administration of the composition to the subject via a route that achieves delivery to the tissue.

In some embodiments, the present disclosure describes therapies that include administration of a composition comprising an agent that is or comprises L-2HG. In some embodiments, the present disclosure describes therapies that include administration of a composition comprising an agent that is or comprises an antagonist of L-2HG.

In some embodiments, the present disclosure describes a therapy that comprises administering a composition comprising, including but not limited to, alpha-ketoglutarate, cell-permeable variants of alpha-ketoglutarate (e.g. dimethyl alpha-ketoglutarate), glutamine, or glutamate. In some embodiments, the present disclosure describes therapies that include administration of a composition comprising an agent that is or comprises an antagonist of alpha-ketoglutarate.

In some embodiments, the present disclosure describes therapies that include administration of a composition comprising an agent that affects the expression or activity of one or more molecules selected from the group consisting of LDHA, MDH1, MDH2, and L-2-hydroxyglutarate dehydrogenase. In some embodiments, the present disclosure describes a therapy comprises administration of an inhibitor of LDHA to the subject via a route that achieves delivery to the tissue. In some embodiments, the present disclosure describes a therapy comprises administration of an activator of L-2-hydroxyglutarate dehydrogenase.

In some embodiments, the present disclosure describes applications involving applying hypoxic conditions. For example, hypoxia may be desirable in some situations such as maintaining pluripotency of stem cells or progenitor cells. In some embodiments, the present disclosure describes systems for promoting tissue hypoxia in a subject that can benefit from hypoxia.

In some embodiments, the present disclosure describes systems for promoting tissue hypoxia in a subject whose L-2HG level is lower compared to a normoxic subject. In some embodiments, the present disclosure describes systems for promoting tissue hypoxia in a subject whose L-2HG level is at most 50% compared to a normoxic reference subject. In some other embodiments, the present disclosure describes systems for promoting tissue hypoxia in a subject whose L-2HG level is at most 40%, at most 30%, at most 20%, at most 10%, or at most 5% compared to a normoxic reference subject.

In some embodiments, the present disclosure describes compositions or systems for maintaining or promoting pluripotency or self-renewal of a cell, a tissue or an organism. In some embodiments, these compositions or systems are for in vivo use. In some embodiments, these compositions and systems are for in vitro use.

In some embodiments, the present disclosure describes compositions or systems for maintaining or promoting pluripotency or self-renewal of a cell. In some embodiments, the cell is a stem cell or a progenitor cell. In some embodiments, these compositions or systems comprise modulating levels of L-2HG in the cells. In some embodiments, the present disclosure describes compositions or systems to modulate levels of L-2HG comprising contacting the cells with L-2HG. In some embodiments, the present disclosure describes compositions or systems for inhibiting L-2-hydroxyglutarate dehydrogenase activity or expression. In some embodiments, the present disclosure describes compositions or systems for promoting LDHA activity or expression. In some embodiments, the present disclosure describes compositions or systems for promoting MDH1 or MDH2 activity or expression. In some embodiments, the present disclosure describes methods to deliver L-2HG to a cell. In some embodiments, the present disclosure describes methods to deplete alpha-ketoglutarate in a cell. In some embodiments, the methods that can be used to maintain or promote pluripotency or self-renewal of a cell or a tissue are applied in cell culture or tissue culture.

In some embodiments, the present disclosure describes that depletion of L-2HG promotes cell differentiation. In some embodiments, the present disclosure describes systems for promoting stem cell differentiation. In some embodiments, these systems comprise contacting a stem cell or a progenitor cell with an effective amount of an inhibitor of LDHA. In some embodiments, these systems comprise contacting a stem cell or a progenitor cell with an effective amount of an activator of L-2-hydroxyglutarate dehydrogenase. In some embodiments, the cell is a cancer stem cell.

In some embodiments, the present disclosure describes the importance of LDHA in L-2HG metabolism. In some embodiments, the present disclosure describes methods for identifying or characterizing an agent useful in inhibiting LDHA activity. In some embodiments, the methods comprise contacting an agent with a sample containing a cell expressing LDHA or a cell-free solution containing LDHA, followed by measuring a level of L-2HG in the sample when the agent is present as compared with when it is absent or when a reference agent is present whose effect on L-2HG level in the sample is known, and determining that the agent is useful in inhibiting LDHA activity if the measured L-2HG level when the agent is present is lower than that when it is absent, is similar to that measured when a reference agent known to decrease L-2HG is present, or is lower than that measured when a reference agent known not to increase L-2HG is present.

In some embodiments, the present disclosure describes the importance of L-2-hydroxyglutarate dehydrogenase in L-2HG metabolism. In some embodiments, the present disclosure describes methods for identifying or characterizing an agent useful in promoting L-2-hydroxyglutarate dehydrogenase activity. In some embodiments, the method comprise contacting an agent with a sample containing a cell expressing L-2-hydroxyglutarate dehydrogenase or a cell-free solution containing L-2-hydroxyglutarate dehydrogenase, measuring a level of L-2HG in the sample when the agent is present as compared with when it is absent or when a reference agent is present whose effect on L-2HG level in the sample is known, and determining that the agent is useful in promoting L-2-hydroxyglutarate dehydrogenase activity if the measured L-2HG level when the agent is present is higher than that when it is absent, is similar to that measured when a reference agent known to increase L-2HG is present, or is higher than that measured when a reference agent known not to decrease L-2HG is present.

In some embodiments, the present disclosure describes the novel finding that L-2HG metabolism is closely linked to epigenetic changes of a cell. For example, the present disclosure describes that L-2HG accumulation promotes histone methylation. In some embodiments, the histone methylation comprises trimethylation of histone 3 lysine 9 (H3K9me3). In some embodiments, the present disclosure describes systems for promoting histone methylation in a cell comprising contacting the cell with a composition comprising L-2HG, an activator of LDHA, an inhibitor of L-2-hydroxyglutarate dehydrogenase, or combinations thereof. On the other hand, in some other embodiments, the present disclosure describes systems for inhibiting histone methylation in a cell comprising contacting the cell with a composition comprising α-KG, an inhibitor of LDHA, or an activator of L-2-hydroxyglutarate dehydrogenase.

In some embodiments, the present disclosure alternatively or additionally describes the novel finding that L-2HG can be used to distinguish cancer phenotypes. For example, the present disclosure demonstrates that L-2HG metabolism affects H3K9me3 staining, which is highly correlated regions of the tumor without IDH1/2 mutation. In some embodiments, the present disclosure describes systems for identifying tumor heterogeneity. In some embodiments, these systems comprising measuring at least one of the following parameters: L-2HG level, alpha-ketoglutarate, expression or activity of LDHA, expression or activity of L-2-hydroxyglutarate dehydrogenase, or H3K9me3. In some embodiments, the tumor is from a patient with glioblastoma.

In some embodiments, the present disclosure describes the novel finding that L-2HG can be used to image hypoxia. In some embodiments, the present disclosure describes systems for administering a composition comprising an agent reacting with L-2HG to a sample or to a subject. In some embodiments, the agent is an antibody that specifically binds to L-2HG. In some embodiments, the agent is conjugated with another moiety that allows it to be visualized by imaging technologies.

In some embodiments, the present disclosure describes compositions or systems that can accurately detect L-2HG. In some embodiments, the present disclosure describes compositions or systems that can distinguish L-2HG from R-2HG. In some embodiments, the present disclosure describes compositions or systems comprising gas chromatography-mass spectrometry, liquid chromatography-mass spectrometry or enzymatic assay. In some embodiments, the present disclosure describes compositions or systems for processing 2-hydroxyglutarate by contacting 2HG with a chiral derivatizing agent.

DEFINITIONS

Figure 1:
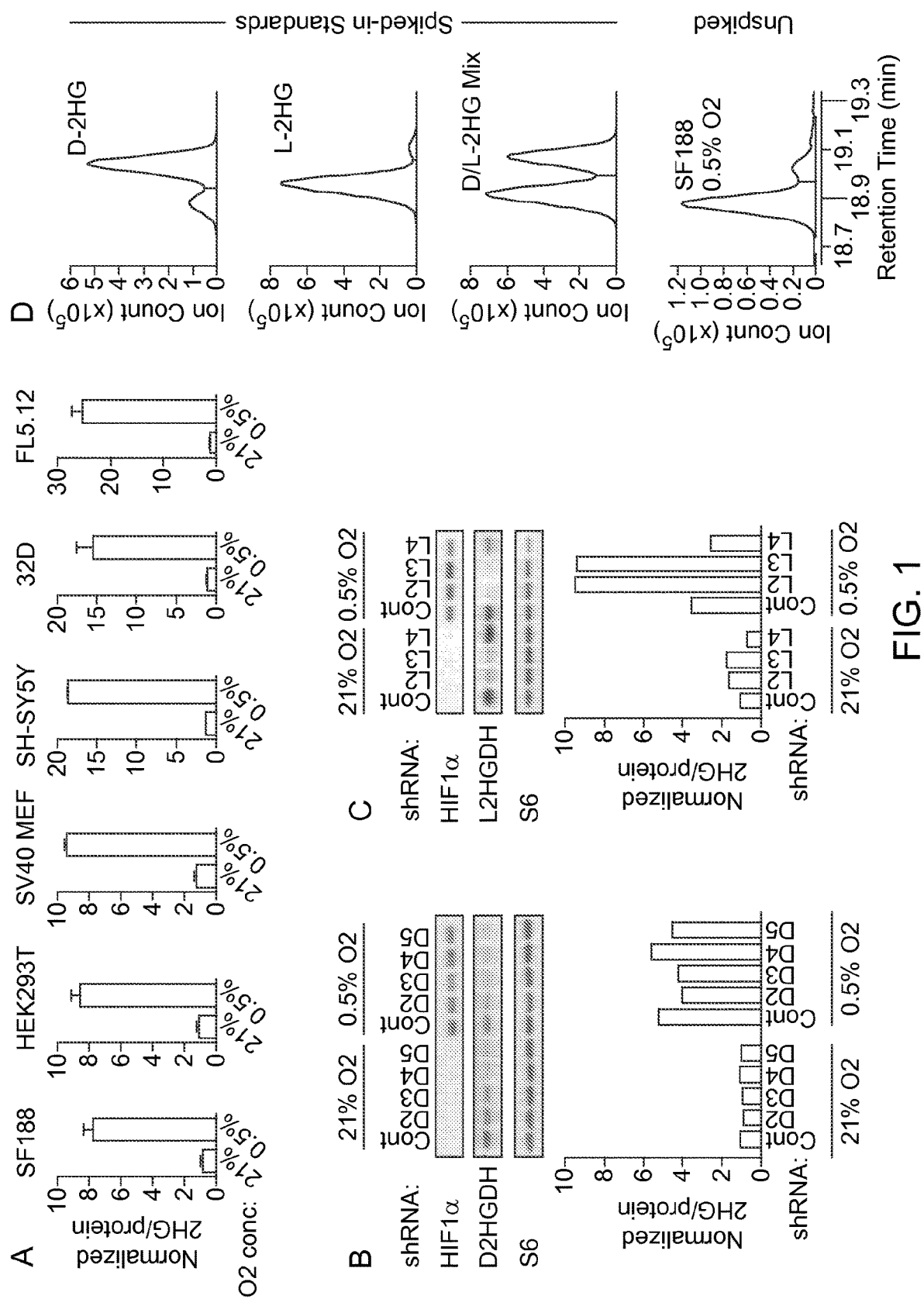
FIG. 1 depicts GC-MS histograms and western blot images showing the production of L-2-Hydroxyglutarate (L-2HG) in response to hypoxia. Panels in (A) are bar graphs showing 2HG levels in different cell types. The indicated cells were cultured for 24 to 48 hr in 21% or 0.5% oxygen ($O_2$). Total intracellular 2HG was measured by gas chromatography-mass spectrometry (GC-MS) and normalized to total protein to control for input. The 2HG level for each cell type in 21% $O_2$ is arbitrarily set to 1 to illustrate fold change. Graphs show mean+/−SD of triplicate samples. Panels in (B and C) are western blots and quantification of these blots showing expression of different proteins. SF188 cells were stably infected with lentiviruses expressing non-targeting shRNA (Cont), shRNAs targeting D2HGDH (D2, D3, D4, D5), or shRNAs targeting L2HGDH (L2, L3, L4). Cells were cultured for 48 hr in 21% or 0.5% $O_2$, and 2HG was measured as in (A). Western blots show expression of HIF1α, D2HGDH, L2HGDH, and S6 protein (loading control). Panels in (D) are GC-MS histograms showing enrichments of ions as function of time. Metabolites from hypoxic SF188 cells were divided into 4 fractions, then spiked with reference standards of D-2HG, L-2HG, a mixture of D- and L-2HG, or left unspiked. Chiral derivatization was performed to allow separation of 2HG enantiomers by GC-MS. For each panel in this figure, representative data from 1 of ≥3 independent experiments are shown. See also FIG. 6.

In this application, unless otherwise clear from context, (i) the term "a" may be understood to mean "at least one"; (ii) the term "or" may be understood to mean "or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Activating agent: As used herein, the term "activating agent," or activator, refers to an agent whose presence or level correlates with elevated level or activity of a target, as compared with that observed absent the agent (or with the agent at a different level). In some embodiments, an activating agent is one whose presence or level correlates with a target level or activity that is comparable to or greater than a particular reference level or activity (e.g., that observed under appropriate reference conditions, such as presence of a known activating agent, e.g., a positive control).

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Agent: The term "agent" as used herein may refer to a compound or entity of any chemical class including, for example, polypeptides, nucleic acids, saccharides, lipids, small molecules, metals, or combinations thereof. In some embodiments, an agent is or comprises a natural product in that it is found in or is obtained from nature. In some embodiments, an agent is or comprises one or more entities that is man-made in that it is designed, engineered, or produced through action of the hand of man or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer or is substantially free of any polymer. In some embodiments, an agent contains at least one polymeric moiety. In some embodiments, an agent lacks or is substantially free of any polymeric moiety.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, or worms. In some embodiments, an animal may be a transgenic animal, genetically-engineered animal, or a clone.

Antagonist: As used herein, the term "antagonist" or an inhibitor refers to an agent that i) inhibits, decreases or reduces the effects of another agent; or ii) inhibits, decreases, reduces, or delays one or more biological events. Antagonists may be or include agents of any chemical class including, for example, small molecules, polypeptides, nucleic acids, carbohydrates, lipids, metals, or any other entity that shows the relevant inhibitory activity. An antagonist may be direct (in which case it exerts its influence directly upon its target) or indirect (in which case it exerts its influence by other than binding to its target; e.g., by interacting with a regulator of the target, for example so that level or activity of the target is altered).

Approximately: As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Associated with: Two events or entities are "associated" with one another, as that term is used herein, if the presence, level or form of one is correlated with that of the other. For example, a particular entity (e.g., polypeptide) is considered to be associated with a particular disease, disorder, or condition, if its presence, level or form correlates with incidence of or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

Combination therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the term "corresponding to" is often used to designate a structural element or moiety in an agent of interest that shares a position (e.g., in three-dimensional space or relative to another element or moiety) with one present in an appropriate reference agent. For example, in some embodiments, the term is used to refer to position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Designed: As used herein, the term "designed" refers to an agent (i) whose structure is or was selected by the hand of man; (ii) that is produced by a process requiring the hand of man; or (iii) that is distinct from natural substances and other known agents.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration or manipulation of data or information, for example utilizing a computer or other processing unit adapted to perform a relevant analysis. In some embodiments, determining involves receiving relevant information or materials from a source. In some embodiments, determining involves comparing one or more features of a sample or entity to a comparable reference.

Diagnostic information: As used herein, "diagnostic information" or "information for use in diagnosis" is information that is useful in determining whether a patient has a disease, disorder or condition or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition (such as cancer), state, staging or characteristic of a disease, disorder or condition as manifested in the subject, information related to the nature or classification of a tumor, information related to prognosis or information useful in selecting an appropriate treatment. Selection of treatment may include the choice of a particular therapeutic (e.g., chemotherapeutic) agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Differentiation: The term "Differentiation" is the process by which an unspecialized ("uncommitted") or less specialized cell acquires the features of a specialized cell such as, for example, a nerve cell or a muscle cell. A differentiated or differentiation-induced cell is one that has taken on a more specialized position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Dosing regimen: (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously (e.g., by infusion) over a predetermined period. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Hypoxia: the term "hypoxia" or "hypoxic condition" as used herein refers to a state or condition in which oxygen in one or more tissues of a mammal is below physiologic levels, e.g., is at a less than optimal level. In some embodiments, hypoxia may result from stress such as aerobic exercise, physical weight pressure, anesthesia, surgery, anemia, acute respiratory distress syndrome, chronic illness, chronic fatigue syndrome, trauma, burns, skin ulcers, cachexia due to cancer and other catabolic states and the like. In some embodiments, hypoxia is or comprises "ischemia" or "ischemic conditions" in which tissues are oxygen-deprived due to reduction in blood flow, as due to constriction in, or blockage of, a blood vessel. Ischemia or ischemic conditions include those caused by coronary artery disease, cardiomyopathy, including alcoholic cardiomyopathy, angioplasty, stenting, heart surgery such as bypass surgery or heart repair surgery ("open-heart surgery"), organ transplantation, prolonged weight pressure on tissues (pressure ulcers or bedsores), ischemia-reperfusion injury which can cause damage to transplanted organs or tissue, and the like. Technologies provided by the present disclosure can be effective, for example to diagnose and/or treat one or more symptoms due to hypoxia, regardless of its underlying cause. For example, in some embodiments, treatments described herein may, for example, increase energy level, strength and/or well-being of a subject suffering from hypoxia even if they do not treat one or more aspects of an underlying condition (e.g., viral or bacterial infection, exposure to bacterial or other toxins, low red-cell counts, aging, cancer, continued exercise, to give but a few examples). In some embodiments, the terms "hypoxia" or "hypoxic condition" refer to a condition of low oxygen content in the blood. In particular embodiments, "hypoxia" or "hypoxic" conditions may be defined by arterial PO2 values less than approximately 80 mm Hg and venous PO2 values less than approximately 30 mm Hg. In some embodiments, "hypoxia" or "hypoxic" conditions may be defined by arterial PO2 values less than approximately 60 mm Hg. In certain embodiments, "hypoxia" or "hypoxic" conditions may be defined by arterial PO2 values less than approximately 50 mm Hg. In a particular embodiment, "hypoxia" or "hypoxic" conditions may be defined by arterial PO2 values between approximately 50-20 mm Hg. Alternatively or additionally, "hypoxia" or "hypoxic" conditions may be differentiated from anoxia, which is defined as an absence or almost complete absence of oxygen from arterial blood or tissues. In some embodiments, type and severity of hypoxia may be defined by absolute or relative quantification or qualification of 2HG. In some embodiments, "hypoxia" or "hypoxic" conditions may be defined by intra-tissue PO2 levels less than about 10 mm Hg. In some embodiments, "hypoxia" or "hypoxic" conditions may be defined by intra-tissue PO2 levels less than about 5 mm Hg. In some embodiments, "hypoxia" or "hypoxic" conditions may be defined by intra-tumor PO2 levels less than about 10 mm Hg. In some embodiments, "hypoxia" or "hypoxic" conditions may be defined by intra-tumor PO2 levels less than about 5 mm Hg. "Hypoxia" or "hypoxic" conditions may be chronic or acute. "Chronic hypoxia", as used herein, may refer to sustained hypoxic conditions that result in a measurable increase in 2HG production. That is, chronic hypoxia may be defined as hypoxic conditions of sufficient duration to allow 2HG to accumulate above baseline levels. In some embodiments, chronic hypoxia is a hypoxic condition of more than 30 minutes, more than 1 hour, more than 2 hours, more than 3 hours, more than 4 hours, more than 5 hours, more than 10 hours, more than 12 hours, more than 24 hours, more than a day, or a week or more in duration. In some embodiments, chronic hypoxia is caused by consumption and depletion of oxygen by tissues or tumor cells between blood capillaries and the hypoxic regions. In contrast to the sustained conditions of chronic hypoxia, acute hypoxia is transient. In some embodiments, acute hypoxia occurs when there a temporary shutdown of vessels or microvasculature in tissues or tumors. In some embodiments, acute hypoxia occurs as a result of fluctuations in red blood cell levels.

Hypoxia-related disease: The term "hypoxia-related disease, disorder or condition" is a disease, disorder or condition associated with (e.g., whose incidence or severity correlates with and/or that is characterized by one or more aspects of) hypoxia. In some particular embodiments, a hypoxia-related disease, disorder or condition may be or comprise, for example, septic shock, ischemic stroke, myocardial infarction, anemia, pulmonary disease, airway obstruction, acute respiratory distress syndrome, pneumonia, pneumothorax, emphysema, congenital heart defects, atherosclerosis, thrombosis, pulmonary embolism, pulmonary edema, asthma, cystic fibrosis, cancer, certain surgical procedures. In some embodiments, a hypoxia-related disease, disorder or condition is associated with stress such as aerobic exercise, physical weight pressure, anesthesia, surgery, anemia, acute respiratory distress syndrome, chronic illness, chronic fatigue syndrome, trauma, burns, skin ulcers, cachexia due to cancer and other catabolic states and the like. In some embodiments, a hypoxia-related disease, disorder or condition is or comprises "ischemia" or "ischemic conditions" in which tissues are oxygen-deprived due to reduction in blood flow, as due to constriction in, or blockage of, a blood vessel. Ischemia or ischemic conditions include those caused by coronary artery disease, cardiomyopathy, including alcoholic cardiomyopathy, angioplasty, stenting, heart surgery such as bypass surgery or heart repair surgery ("open-heart surgery"), organ transplantation, prolonged weight pressure on tissues (pressure ulcers or bedsores), ischemia-reperfusion injury which can cause damage to transplanted organs or tissue, and the like.

Marker: A marker, as used herein, refers to an entity or moiety whose presence or level is a characteristic of a particular state or event. In some embodiments, presence or level of a particular marker may be characteristic of presence or stage of a disease, disorder, or condition. To give one example, in some embodiments, the term refers to a metabolite, e.g., L-2HG, that is characteristic of a particular hypoxia-induced injury, etc. To give another example, in some embodiments, the term refers to a gene expression product, e.g., LDHA, that is characteristic of a particular hypoxia-induced injury. In some embodiments, the marker may be associated with a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors, e.g., glioblastoma. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Mass spectrometry: Mass spectrometry refers to method using a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these.

Metabolite: As used herein, "metabolite" refers to any substance produced or used during a physical or chemical processes within the body that creates or uses energy, such as: digesting food and nutrients, eliminating waste through urine and feces, breathing, circulating blood, and regulating temperature. The term "metabolic precursors" refers to compounds from which the metabolites are made. The term "metabolic products" refers to any substance that is part of a metabolic pathway (e.g., metabolite, metabolic precursor).

Modulator: The term "modulator" is used to refer to an entity whose presence or level in a system in which an activity of interest is observed correlates with a change in level or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Normoxic: As used herein, the term "normoxic" refers to serum or tissue PO2 levels that are not chronically or acutely hypoxic. When used to modify the term "individual" or "subject", the term refers to an individual or group of individuals who does not have a chronic or acute hypoxia. For example, in particular embodiments, normoxic individuals have an arterial PO2 of between approximately 80-100 mm Hg or a venous PO2 of approximately 30-50 mm Hg. "Normoxia" or "Normoxic" may alternatively or additionally be defined by in vivo or in vitro atmospheric oxygen tension of approximately 21%. In some embodiments, normoxic levels are established by consideration of levels present across or within a population of individuals who do not have a chronic or acute hypoxia. For example, in some embodiments, normoxic levels represent an average, median, or mean value of levels across or within such a population, typically showing statistical significance. In some embodiments, "normoxic" conditions may be defined by intra-tissue PO2 levels greater than about 10 mm Hg. In some embodiments, Nutrients: As used herein, the term "nutrients" refers to: amino acids and peptides, vitamins, nucleotides, fatty acids, carbohydrates, minerals and other substances or materials that contribute to the well-being of a cell, a tissue or an organism.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: The term "pharmaceutically acceptable" as used herein, refers to agents that, within the scope of sound medical judgment, are suitable for use in contact with tissues of human beings or animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates or polyanhydrides; and other non-toxic compatible substances employed in pharmaceutical formulations.

Prevention: The term "prevention", as used herein, refers to a delay of onset, or reduction in frequency or severity of one or more symptoms of a particular disease, disorder or condition. In some embodiments, prevention is assessed on a population basis such that an agent is considered to "prevent" a particular disease, disorder or condition if a statistically significant decrease in the development, frequency, or intensity of one or more symptoms of the disease, disorder or condition is observed in a population susceptible to the disease, disorder, or condition.

Progenitor cell: As used herein, the term "progenitor cell" refers to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, GC-MS, or histology. The exact response criteria can be selected in any appropriate manner, provided that when comparing groups of tumors or patients, the groups to be compared are assessed based on the same or comparable criteria for determining response rate. One of ordinary skill in the art will be able to select appropriate criteria.

Risk: As will be understood from context, a "risk" of a disease, disorder or condition is a degree of likelihood that a particular individual will develop the disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition. In some embodiments a reference sample or group of reference samples are from individuals comparable to a particular individual. In some embodiments, relative risk is 0, 1, 2, 3, 4, 5, 6, 7, 8, 9, 10 or more.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, or excretions; or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation or purification of certain components, etc.

Small molecule: As used herein, the term "small molecule" means a low molecular weight organic or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic.

Specific: The term "specific", when used herein with reference to an agent or entity having an activity, is understood by those skilled in the art to mean that the agent or entity discriminates between potential targets or states. For example, an agent is said to bind "specifically" to its target if it binds preferentially with that target in the presence of competing alternative targets. In some embodiments, the agent or entity does not detectably bind to the competing alternative target under conditions of binding to its target. In some embodiments, the agent or entity binds with higher on-rate, lower off-rate, increased affinity, decreased dissociation, or increased stability to its target as compared with the competing alternative target(s).

Stress-induced disorders: The term "stress-induced disorders" include those which arise when an organism is placed in an environment that disrupts its homeostasis. Events such as illness, disease, life-threatening events, starvation, fatigue, hypoxia, etc. are all understood to be stressors on an organism. In some embodiments, the stress-induced disorders are caused by hypoxia.

Stem cells: The term "stem cells" include but are not limited to undifferentiated cells defined by their ability at the single cell level to both self-renew and differentiate to produce progeny cells, including self-renewing progenitors, non-renewing progenitors, and terminally differentiated cells. For example, "stem cells" may include (1) totipotent stem cells; (2) pluripotent stem cells; (3) multipotent stem cells; (4) oligopotent stem cells; and (5) unipotent stem cells.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. A subject can be a patient, which refers to a human presenting to a medical provider for diagnosis or treatment of a disease. In some embodiments, a subject is an individual to whom therapy is administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion or proceed to completeness or achieve or avoid an absolute result. The term "substantially" is therefore used herein to capture the potential lack of completeness inherent in many biological and chemical phenomena.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, or condition. In some embodiments, an individual who is susceptible to a disease, disorder, or condition is an individual who has been exposed to conditions associated with development of the disease, disorder, or condition. In some embodiments, a risk of developing a disease, disorder, or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, or reduce incidence of one or more symptoms or features of a disease, disorder, or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically effective amount: as used herein, is meant an amount that produces the desired effect for which it is administered. In some embodiments, the term refers to an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated or administered in a single dose. In some embodiments, a therapeutically effective agent may be formulated or administered in a plurality of doses, for example, as part of a dosing regimen.

Treatment: As used herein, the term "treatment" ("treat" or "treating") refers to any administration of a substance (e.g., anti-receptor tyrosine kinases antibodies or receptor tyrosine kinase antagonists) that partially or completely alleviates, ameliorates, relives, inhibits, delays onset of, reduces severity of, or reduces incidence of one or more symptoms, features, or causes of a particular disease, disorder, or condition (e.g., cancer). Such treatment may be of a subject who does not exhibit signs of the relevant disease, disorder or condition or of a subject who exhibits only early signs of the disease, disorder, or condition. Alternatively or additionally, such treatment may be of a subject who exhibits one or more established signs of the relevant disease, disorder or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

Unit dose: The expression "unit dose" as used herein refers to an amount administered as a single dose or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components Alternatively or additionally to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs or additional therapies used in combination or coincidental with specific compound(s) employed, and like factors well known in the medical arts.

DETAILED DESCRIPTION OF CERTAIN EMBODIMENTS

The present invention provides, among other things, compositions or systems for the diagnosis or treatment of conditions associated with hypoxia. In some embodiments, the present disclosure also describes compositions or systems for modulating cell pluripotency or differentiation.

Various aspects of the invention are described in detail in the following sections. The use of sections is not meant to limit the invention. Each section can apply to any aspect of the invention. In this application, the use of "or" means "or" unless stated otherwise.

Hypoxia and Stress-Induced Metabolism

Stress, such as hypoxia, infection, starvation, temperature, toxicity and the like significantly affects metabolism of the cells and contributes to major diseases. As shown in the examples below, embodiments of the present invention encompass the study of stress-induced metabolism. In some embodiments, stress is caused by hypoxia.

Hypoxia is involved in a variety of disease processes, and is responsible for significant tissue damage when left untreated. A constant, uninterrupted supply of oxygen is essential to sustain life. Hypoxia is a condition of low oxygen content in the blood or tissues resulting from an imbalance between oxygen supply and demand. Several different subtypes of hypoxia are known. For example, anemic hypoxia is due to a decreased concentration of functional hemoglobin or a reduced number of red blood cells. Hypoxic hypoxia results from a defective mechanism of oxygenation in the lungs, which may be caused by low tension of oxygen, abnormal pulmonary function, airway obstruction, or a right-to-left shunt in the heart. Oxygen affinity hypoxia is due to a reduced ability of hemoglobin to reduce oxygen. Tissue or cellular hypoxia is caused by interrupted coronary blood flow or a reduction in arterial blood oxygen partial pressure (PO2).

Given the requirement of oxygen to sustain life, organisms have evolved diverse mechanisms to cope with both acute and chronic decreases in oxygen availability; i.e., with acute and chronic hypoxia. For multicellular organisms, particularly mammals, these mechanisms include erythropoiesis, angiogenesis and adaptive metabolic changes designed to maintain cellular activity at a minimum acceptable level. Acute hypoxia occurs in situations such as stroke, septic shock, myocardial infarction, and during surgical procedures. Chronic hypoxia, on the other hand, is associated with anemia, congestive heart failure, pulmonary disease, congenital heart disease, as well as cancer.

However, it is to be understood that the above list of hypoxia-related diseases is not a complete list of all conditions that hypoxia is involved. A person skilled in the art knows that the compositions or systems of the present disclosure can be applied to any hypoxia-related disease, disorder or condition, including those not on the above list.

L-2HG Metabolism Under Hypoxic Conditions

It is known that nutrients and metabolic intermediates can influence cellular responses to physiologic perturbations in addition to fueling cellular growth and proliferation (Vander Heiden et al., 2009; Ward and Thompson, 2012). The present disclosure, among other things, identifies L-2HG induction as a novel cellular metabolic response to stress imposed by hypoxia.

The present disclosure significantly expands on prior knowledge of 2HG and demonstrates L-2HG as a novel metabolite that controls certain functions of cellular metabolism. Nutrients and metabolites influence fundamental cellular processes (Kaelin and McKnight, 2013; Vander Heiden et al., 2009). The relationship between α-KG and 2HG has been proposed as one such example. For example, α-KG serves as an essential substrate for approximately 70 different enzymes involved in such diverse functions as demethylation of histones and DNA, regulation of HIF1α stability, and maturation of collagen (Losman and Kaelin, 2013). By coupling these enzymatic processes to α-KG availability, the metabolic fitness of the cell can be intimately linked to important cellular 'decisions' such as lineage differentiation and adaptation to environmental stressors. Inhibition of α-KG-dependent enzyme activity by the 'oncometabolite' D-2HG appears to represent the primary mechanism whereby oncogenic mutations in IDH1/2 disrupt normal cellular physiology (Kaelin and McKnight, 2013; Losman and Kaelin, 2013; Ward and Thompson, 2012).

2-hydroxyglutarate (2HG) is a chiral molecule that can exist in either the D- or L-stereoisomer. Compared to L-2HG, D-2HG has been the subject of intense research. Mutations in isocitrate dehydrogenase 1 or 2 (IDH1/2) result in production of the "oncometabolite" D-2-hydroxyglutarate (D-2HG, also known as (R)-2-hydroxyglutarate). D-2HG blocks differentiation of malignant cells by functioning as a competitive inhibitor of alpha-ketoglutarate (α-KG) dependent enzymes, including Jumonji family histone lysine demethylases.

In contrast to the intensive research efforts focused on elucidating the role of D-2HG in the molecular pathogenesis of IDH1/2-mutant malignancies, less attention has been paid to the potential roles for controlled production and elimination of D-2HG and L-2HG in normal cellular physiology (Kranendijk et al., 2012). Although cancer-associated IDH1/2 mutations exclusively produce D-2HG, biochemical studies have demonstrated that L-2-hydroxyglutarate (L-2HG, also (R)-2-hydroxyglutarate) functions as a more potent inhibitor of α-KG-dependent enzymes. However, biologic sources or activities of L-2HG remain unknown. Possible physiologic roles for both 2-hydroxyglutarate enantiomers are suggested by the existence of evolutionarily conserved "waste disposal" enzymes, known as D2HGDH (D-2-hydroxyglutarate dehydrogenase) and L2HGDH (L-2-hydroxyglutarate dehydrogenase), whose sole function is to convert D-2HG or L-2HG to α-ketoglutarate, respectively.

The present disclosure identifies, among other things, L-2HG induction as a novel cellular metabolic response to the environmental stress imposed by hypoxia. For example, the inventors discovered that production of L-2HG in hypoxia occurs independently of IDH1/2, instead arising via promiscuous enzymatic reduction of α-KG primarily by LDHA.

The present disclosure demonstrates that loss-of-function of IDH1 or IDH2 did not impair production of L-2HG in hypoxic condition in multiple types of cells. Thus, IDH1/2 enzymes are likely incapable of reducing α-KG to L-2-hydroxyglutarate due to steric constraints on substrate binding. The inventors tested the requirement for metabolic enzymes whose primary catalytic activities involve reduction of α-ketoacid substrates to L-hydroxyl acids with structural similarities to α-KG and L-2HG Strikingly, however, the present disclosure demonstrates that lactate dehydrogenase A (LDHA) is the major enzyme required for the production of hypoxia-induced L-2HG. The present disclosure identifies a partial contribution from MDH1 and MDH2 to hypoxia-induced L-2HG. These observations were confirmed when combined ablation of LDHA and MDH2 also resulted in a near total abrogation of hypoxia-induced L-2HG. The present disclosure demonstrates from multiple lines of evidence the role of LDHA in L-2HG metabolism, including, for example, genetic manipulation (e.g., loss of function) and structural biology. For example, the inventors discovered that the active site of LDHA can accommodate reduction of α-KG to L-2HG. Collectively, these findings from the present disclosure suggest that hypoxic cells can produce L-2HG from reduction of glutamine-derived α-KG in the cytoplasm via promiscuous substrate usage by LDHA, with a smaller contribution from cytosolic MDH1 and mitochondrial MDH2.

Hypoxia-induced L-2HG represents a molecular mechanism whereby cells might repress α-KG-dependent processes (e.g. demethylation of H3K9me3) when faced with limited oxygen availability. The inventors discovered that L-2HG can suppress α-KG-dependent reversal of hypoxic adaptation. Thus, the present disclosure demonstrates, among other things, that hypoxia-induced L-2HG represents a means through which cells can maintain repression of α-KG-dependent processes that might counteract hypoxic adaptation. In some embodiments, the present disclosure demonstrates that hypoxia-induced accumulation of L-2HG is glutamine dependent, indicating a link between glutamine-dependent L-2HG production in hypoxia and sustained HIF1α induction.

In some embodiments, the present disclosure describes that environmental stress, particularly hypoxia, triggers cellular mechanisms that regulate L-2HG. Therefore, the present disclosure elucidated the molecular mechanisms by which hypoxia affects L-2HG metabolism.

Diagnosing Hypoxia and Hypoxia-Induced Injury

The present invention, among other things, provides novel systems of diagnosis for hypoxia or hypoxia-induced injuries. In some embodiments, the present disclosure describes systems for diagnosing a hypoxia-related disease, disorder or condition. It has been determined in accordance with the present invention that L-2HG, a rare metabolite found at trace amounts in mammalian cells and body fluids under normal conditions, is reproducibly elevated significantly under conditions of inadequate oxygen supply and is sufficient to serve as a biomarker for hypoxia or hypoxia-induced injuries.

It has been determined in accordance with the present invention that L-2HG arises from the non-carboxylating reduction of the citric acid cycle intermediate α-ketoglutarate through the action of LDHA. The present disclosure demonstrates that MDH1 or MDH2 also contributes to this process. Under normal conditions, the extent of this reaction to produce L-2HG is minimal, and the L-2HG that is produced does not substantially accumulate due to the enzymatic activity of L-2HG dehydrogenase, which functions to oxidize L-2HG back to α-ketoglutarate. However, as disclosed herein, after hypoxic conditions, the normal oxidative metabolism of α-ketoglutarate is suppressed in human cells and α-ketoglutarate preferentially undergoes reductive metabolism that leads to the accumulation of L-2HG.

L-2HG elevation occurs with hypoxia and reflects alterations in metabolism at the cellular level. Known situations independent of hypoxia where serum total 2HG (both L- and D-2HG) is elevated are limited to rare inborn errors of metabolism involving germline genetic mutations, or myeloid hematologic malignancies with specific somatic mutations in the IDH1/2 genes. These patients are rare relative to the number presenting with cardiopulmonary disease or tissue hypoxia, and their symptoms are distinctive and non-overlapping. Therefore, the risks of false positives with testing L-2HG for chronic hypoxia are likely to be low.

As discussed in the Examples section, L-2HG has been discovered to be a biomarker of hypoxia and can be used to diagnose hypoxia. L-2HG levels may be detected by any method known to those of skill in the art. Non-limiting examples of various detection methodologies are discussed below. The present invention provides the particular insight that methodologies such as gas chromatography-mass spectrometry ("GC-MS"), liquid chromatography-mass spectrometry ("LC-MS"), enzymatic assays and immune-based methods may be used to measure L-2HG levels. The present invention provides that chiral derivatization can be used to distinguish L-2HG from D-2HG.

In some embodiments, the present disclosure describes methods for diagnosing hypoxia and hypoxia-induced injuries. In certain embodiments, measuring levels of L-2HG in blood or tissue could serve as a sensitive and specific biomarker for tissue hypoxia, with potential clinical relevance for the diagnosis or monitoring of a hypoxia-related disease, disorder or condition.

The present invention provides, among other things, hypoxia can be diagnosed by expression or activity of certain L-2HG-related enzymes, including but not limited to, LDHA, MDH1, MDH2, or L-2HG dehydrogenase. In embodiments where these enzymes are measured, the additional markers may be measured by any method known to those of skill in the art; for example, immunoassays (e.g., Western blotting), hybridization (e.g. Northern blotting), RT-PCR, and mass spectrometry). For example, in a particular embodiment, L-2HG levels may be assayed by GC-MS and evaluated or correlated in combination with nucleic acid- or immunoassay-based measures of LDHA, MDH1, MDH2, or L-2HG dehydrogenase.

In some embodiments, the present disclosure describes that levels of L-2HG from a subject can be compared to those from a normoxia control subject. In some embodiments, the present disclosure describes that levels of L-2HG from a subject can be compared to those from a patient with diagnosed acute hypoxia or chronic hypoxia.

The present disclosure alternatively or additionally describes systems for diagnosing hypoxia-induced injury in a patient. Hypoxia-induced injuries that are not symptomatic or sub-symptomatic are often difficult to clinically diagnose. However, measuring L-2HG levels from a sample could give indication for hypoxia-induced injury in a subject.

The present disclosure describes parameters against which L-2HG levels can be compared, for example, with diagnosing or treating hypoxia or hypoxia-induced injury. To give but one example, in some embodiments, the present disclosure describes treatment of hypoxia by administration of a hypoxia therapy to a subject whose L-2HG level is elevated compared to that of a normoxic reference subject. In some embodiments, an elevated level of L-2HG is at least two-fold, at least three-fold, at least four-fold, at least five-fold, at least six-fold, at least seven-fold, at least eight-fold, at least nine-fold, at least ten-fold, or even higher as compared with that observed for a normoxic subject.

In some embodiments, the present disclosure describes that L-2HG could be used as a alone for diagnosing hypoxia or hypoxia-induced injury. In some embodiments, the present disclosure describes methods that use L-2HG as part of a biomarker set in diagnosis. For example, in some embodiments, the present disclosure describes method that measure at least two biomarkers in a sample from the subject, wherein one of the at least two biomarkers is L-2HG.

In some embodiments, a hypoxia marker as described herein is measured in a patient sample. In some embodiments a sample may be or comprise a tissue sample, for example from a heart, artery, brain, tumor, or combinations thereof. In some embodiments, a sample may be or comprise blood, urine, serum, lymph or cerebrospinal fluid. In some embodiments, a sample may be or comprise a venous blood sample.

Those of skill in the art will appreciate that hypoxic states may be found both within the tissue with hypoxic injury, e.g., tumor, and in adjacent or nearby tissues. For example, chronic hypoxia may be caused by consumption and depletion of oxygen by tumor cells between blood capillaries and the hypoxic regions. Thus, samples for measurement of L-2HG levels to determine whether a tissue or a subject is hypoxic may be obtained from a tumor itself or nearby tissue.

In some embodiments, the present disclosure provides technologies for stratifying patient populations (e.g., with respect to their candidacy for treatment with hypoxia therapy), or for monitoring effectiveness of or modulating particular therapy as administered to one or more subjects.

In some embodiments, the present disclosure describes the use of L-2HG as a biomarker for clinical assessment of therapeutic interventions. For example, clearance of L-2HG from the blood can be used as a biomarker to assess adequacy of therapeutic intervention for a hypoxia-related disease, disorder or condition. Identification or selection of appropriate treatment, determining if a patient has positive response to a treatment or optimization of the treatment can be guided using the information obtained in these methods.

In some embodiments, the present invention provides methods for evaluating the effectiveness of a therapy, monitoring responsiveness to therapy, prognosis for disease course, and measurement of disease progression in a subject. For example, levels of suitable biomarkers (e.g., L-2HG, or expression/activity of LDHA) determined for a biological sample obtained from the subject from one or more time points are compared to the levels from the subject from one or more other time points.

Modulating L-2HG

It is contemplated that provided methods and compositions may be used to treat any of a variety of hypoxia-related diseases, disorders or conditions. Since L-2HG has been shown to be a potent inhibitor of enzymes involved in collagen maturation (Koivunen et al, Nature 2012), hypoxic induction of L-2HG might be involved in tissue repair and neovascularization after ischemic tissue injury. For example, the present disclosure describes that therapeutic manipulation of L-2HG production, e.g., modulation of LDHA activity (the primary source of hypoxic L-2HG), exogenous supplementation of L-2HG, etc., might be of benefit in conditions such as myocardial infarction or ischemic stroke.

Therapeutic uses include administration of an agent that modulate L-2HG metabolism alone or in combination with other treatments that is known to be used in treating such hypoxia-related disease, disorder or condition. For example, in some embodiments, for a patient with cancer, therapeutic uses include administration of an agent that modulate L-2HG metabolism alone or in combination with a cancer therapy, such as chemotherapy, etc.

In some embodiments, the present disclosure describes novel compositions or systems for treating hypoxia or hypoxia-induced injuries. In some embodiments, the present disclosure describes compositions or systems for treating hypoxia-related diseases, disorders or conditions. A person skilled in the art would know that compositions or systems described by the present disclosure can be used to treat any hypoxia-related disease, disorder or condition.

In some embodiments, the present disclosure describes therapies that modulate L-2HG levels in a tissue or systemically. In some embodiments, the present disclosure describes therapies that increase the level of L-2HG in the subject. In some embodiments, the present disclosure describes therapies that decrease the level of L-2HG in the subject.

In some embodiments, the present disclosure describes therapies that include administration of a composition comprising an agent that modulate L-2HG metabolism. In some embodiments, the present disclosure describes therapies that include administration of the composition to the subject via a route that achieves delivery to the tissue.

In some embodiments, the present disclosure describes therapies that include administration of a composition comprising an agent that is or comprises L-2HG. In some embodiments, the present disclosure describes therapies that include administration of a composition comprising an agent that is or comprises an antagonist of L-2HG.

In some embodiments, the present disclosure describes a therapy that comprises administering a composition comprising, including but not limited to, alpha-ketoglutarate, cell-permeable variants of alpha-ketoglutarate (e.g. dimethyl alpha-ketoglutarate), glutamine, or glutamate. In some embodiments, the present disclosure describes therapies that include administration of a composition comprising an agent that is or comprises an antagonist of alpha-ketoglutarate.

In some embodiments, the present disclosure describes targeting agents for modulating L-2HG metabolism. In principle, any agent whose level, form, or activity correlates with or modulates (e.g., inhibits or enhances) a feature of L-2HG metabolism can be an L-2HG targeting agent, at least for certain embodiments as described herein. In some embodiments, the present disclosure describes therapies that include administration of a composition comprising an agent that affects the expression or activity of one or more molecules selected from the group consisting of LDHA, MDH1, MDH2, and L-2-hydroxyglutarate dehydrogenase. In some embodiments, the present disclosure describes a therapy comprises administration of an inhibitor of LDHA to the. In some embodiments, the present disclosure describes a therapy comprises administration of an activator of L-2-hydroxyglutarate dehydrogenase.

In some embodiments, an agent that targets L-2HG metabolism as described herein is or comprises a small molecule. In some embodiments, an agent that targets L-2HG metabolism as described herein is or comprises a polypeptide. In some embodiments, an agent that targets L-2HG metabolism as described herein is or comprises a nucleic acid. In some embodiments, an agent that targets L-2HG metabolism as described herein is or comprises a glycan. In some embodiments, an agent that targets L-2HG metabolism as described herein is or comprises a lipid. In some embodiments, an agent that targets L-2HG metabolism as described herein is or comprises an antibody agent (e.g., that binds to a component of the L-2HG metabolism machinery). In some embodiments, an agent that targets L-2HG metabolism as described herein is or comprises a nucleic acid agent (e.g., an antisense, shRNA or siRNA agent) (e.g., that binds to a component of the L-2HG metabolism machinery or to a gene or gene product that encodes it or is complimentary such. In some embodiments, a targeting agent is or is associated with a detectable moiety. In some embodiments, a targeting agent is associated with a therapeutic moiety.

In general, the present disclosure demonstrates the desirability and effectiveness of treating certain hypoxia-induced injuries by targeting L-2HG metabolism. Those skilled in the art will appreciate that any of a variety of approaches may be utilized to effectuate such targeting.

In accordance with various embodiments of systems for the invention, an agent that targets L-2HG or enzymes that modulate L-2HG metabolism can be administered to a subject alone, or as a component of a composition or medicament, as described herein.

In some embodiments, a provided agent can be formulated with a physiologically acceptable carrier or excipient to prepare a pharmaceutical composition. In some embodiments, a carrier utilized in such a pharmaceutical composition, or the composition itself, can be sterile. In some embodiments, a pharmaceutical composition is formulated for a specific mode of administration. Systems for formulating compositions are known in the art (see, e.g., Remington's Pharmaceuticals Sciences, 17$^{th}$ Edition, Mack Publishing Co., (Alfonso R. Gennaro, editor) (1989)).

A composition or medicament, if desired, can contain one or more of protein (esp. albumin), nanoparticles, microparticles, liposomes, and micelles, for example as carriers, particularly for delivery of fatty acids or lipids.

A composition described herein may be administered by any appropriate route. In some embodiments, a composition is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, a composition is administered intravenously. In some embodiments, a composition is administered orally. In some embodiments, a composition is administered by direct administration to a target tissue, such as heart or muscle (e.g., intramuscular), tumor (intratumorallly), nervous system (e.g., direct injection into the brain; intraventricularly; intrathecally). Alternatively or additionally, a composition can be administered by inhalation, parenterally, intradermally, transdermally, or transmucosally (e.g., orally or nasally). More than one route can be used concurrently, if desired.

In some embodiments, a composition is administered in a therapeutically effective amount or according to a dosing regimen that is correlated with a particular desired outcome.

Particular doses or amounts to be administered in accordance with the present disclosure may vary, for example, depending on the nature or extent of the desired outcome, on particulars of route or timing of administration, or on one or more characteristics (e.g., weight, age, personal history, genetic characteristic, lifestyle parameter, or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a particular endpoint, e.g., tumor, myocardial infarction, etc.

In some embodiments, certain components of L-2HG metabolism machinery are targeted (e.g., LDHA), for example through use of an agent that interacts directly with such component, or otherwise modulates its level or activity.

In various embodiments, a therapeutic modality targeting L-2HG metabolism as described herein is administered over a time period of at least 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed, e.g., tumor shrinkage is observed, or heart function improves.

Identification and/or Characterization of L-2HG Modulating Agents

In some embodiments, the present invention provides methods and systems for identifying or characterizing L-2HG agents or protocols. In some embodiments, provided methods and systems include administering one or more candidate L-2HG modulating agents or protocols to a cell, a tissue or an organism and assaying for L-2HG response. In some embodiments, the cell or the tissue is in vitro. In some embodiments, the cell or the tissue is in vivo. In some embodiments, candidate L-2HG modulating agents or protocols are applied to a cell free system. In some embodiments, candidate L-2HG modulating agents or protocols are applied as a component of a high throughput screening system.

In some embodiments, provided methods and systems select L-2HG enhancing agents. In some embodiments, provided methods and systems select L-2HG inhibiting agents.

In some embodiments, provided methods and systems include administering one or more candidate L-2HG modulating agents or protocols to a cell, a tissue or an organism and assaying for down-stream effects of L-2HG metabolism. In some embodiments, the down-stream effect of L-2HG metabolism is trimethylation of histone 3 lysine 9. In some embodiments, the down-stream effect of L-2HG metabolism is trimethylation of histone 3 lysine 27.

In some embodiments, a candidate L-2HG enhancing agent or protocol is considered a L-2HG enhancing agent or protocol if administration to a cell, a tissue or an organism results in an increase in the parameter measured, e.g., L-2HG, by 30%, 40%, 50%, 60%, 70%, 80%, 90%, or more as compared to a similar cell, tissue or an organism that was not exposed to the agent(s) or protocol(s).

In some embodiments, a candidate L-2HG inhibiting agent or protocol is considered a L-2HG inhibiting agent or protocol if administration to a cell, a tissue or an organism results in a reduction in the parameter measured, e.g., L-2HG, by 30%, 40%, 50%, 60%, 70%, 80%, 90%, or more as compared to a similar cell, tissue or an organism that was not exposed to the agent(s) or protocol(s).

Diagnosing Cancer Phenotype According to L-2HG Metabolism

It is contemplated that provided methods and compositions may be used to detect or image hypoxia in a tissue. In some embodiments, the tissue is a tumor. In some embodiments, hypoxia is detected or imaged by L-2HG, a certain enzyme regulating L-2HG metabolism, or a certain down-stream epigenetic change effected by L-2HG, or combinations thereof. In some embodiments, hypoxia is detected or imaged by L-2HG. In some embodiments, hypoxia is detected or imaged by LDHA. In some embodiments, hypoxia is detected or imaged by H3K9me3. In some embodiments, hypoxia is detected or imaged by at least one additional method. In some embodiments, this additional method is a mutation of a gene.

The present disclosure demonstrates that L-2HG directly modulate epigenetic signaling, which play an important role in cancer cell biology. Biochemically, both D-2HG and L-2HG have been reported to inhibit the Jumonji family histone lysine demethylase KDM4C, resulting in aberrant accumulation of trimethylated histone 3 lysine 9 (H3K9me3) and impairment of normal cellular differentiation (Chen et al., 2013; Chowdhury et al., 2011; Kats et al., 2014; Lu et al., 2012; Rohle et al., 2013; Sasaki et al., 2012). For example, in glioblastomas, IDH1/2 mutation is associated with diffuse increases in H3K9me3 throughout the tumor, whereas H3K9me3 shows regional variations in tumors without IDH1/2 mutation (Venneti et al., 2013a). These data suggest that the variability in H3K9me3 staining in IDH1/2-wildtype glioblastomas might correlate with regions of hypoxia.

In the present disclosure, the inventors tested correlation between HIF1α expression and H3K9me3 by immunohistochemistry using human glioblastoma samples wildtype for IDH1/2 and found that HIF1α expression and H3K9me3 were highly statistically correlated. These observations suggested that hypoxia-induced L-2HG might mediate the enhancement of H3K9me3 observed in vascularly compromised regions of human glioblastoma. The inventors discovered that when hypoxia-induced L-2HG was abrogated, there was a substantial reduction in hypoxia-induced H3K9me3. Conversely, ablation of L2HGDH—with consequent increase of hypoxia-induced L-2HG—resulted in increased H3K9me3. The inventors observed a similar pattern, albeit less robust, with H3K27me3. Therefore, the present disclosure establishes that L-2HG promotes the formation of epigenetic modifications (e.g. trimethylation of H3K9, and H3K27).

The present disclosure describes that by using biopsies from patients with glioblastomas, the inventors discovered that hypoxic induction of L-2GH contributes to the development of epigenetic heterogeneity in this tumor type. Tumor cells that are under the influence of hypoxia would develop different phenotypes compared to tumor cells without such a condition. Thus, the level of L-2HG, or the level or activity of other factors regulating L-2HG, can be used as an indicator for distinguishing cancer phenotype.

In some embodiments, the present disclosure demonstrates that L-2HG metabolism affects H3K9me3 staining, which is highly correlated regions of the tumor without IDH1/2 mutation. In some embodiments, the present disclosure describes systems for distinguishing tumor phenotypes or identifying tumor heterogeneity using expression or activity of LDHA, alpha-ketoglutarate, or H3K9me3. In some embodiments, the tumor is from a patient with glioblastoma.

Cancers may be screened to detect mutations as described herein using any of a variety of known technologies. In some embodiments, particular mutations or expression thereof, are detected at the nucleic acid level (e.g., in DNA or RNA). In some embodiments, such mutations, or expression thereof, are detected at the protein level (e.g., in a sample comprising polypeptides from cancer cells, which sample may be or comprise polypeptide complexes or other higher order structures including but not limited to cells, tissues, or organs).

In some particular embodiments, detection involves nucleic acid sequencing. In some embodiments, detection involves whole exome sequencing. In some embodiments, detection involves immunoassay. In some embodiments, detection involves use of amicroarray. In some embodiments, detection involves massively parallel exome sequencing sequencing. In some embodiments, mutations may be detected by genome sequencing. In some embodiments, detection involves RNA sequencing. In some embodiments, detection involves standard DNA or RNA sequencing. In some embodiments, detection involves mass spectrometry.

In some embodiments, detection involves next generation sequencing (DNA and/or RNA). In some embodiments, detection involves genome sequencing, genome resequencing, targeted sequencing panels, transcriptome profiling (RNA-Seq), DNA-protein interactions (ChIP-sequencing), and/or epigenome characterization.

In some embodiments, detection involves using a technique such as ELISA, Western Transfer, immunoassay, mass spectrometry, microarray analysis, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

Systems and Protocols Modulating Cell Pluripotency and Self-Renewal

The present disclosure demonstrates, among other things, that hypoxia-induced levels of L-2HG result in enhanced repressive histone methylation. While the oncogenic production of D-2HG by IDH1/2 mutations leads to a cancer-promoting block to differentiation, hypoxia-induced L-2HG might function as a physiologic regulator of stem/progenitor cell differentiation. Hypoxia-induced L-2HG might account, at least in part, for the importance of both hypoxic niches and LDHA for maintaining the self-renewal of various stem cell populations. Specifically, the present disclosure describes that normal stem cells residing in hypoxic niches may produce sufficient L-2HG to maintain the silencing of genes required for differentiation, thus maintaining a progenitor/stem cell fate.

Targeting L-2HG to Maintain the Pluripotency and Self-Renewal of Stem Cells and Progenitor Cells.

Hypoxic induction of L-2HG may be involved in maintaining the pluripotency and self-renewal of normal stem cells, including embryonic, hematopoietic, or organ stem cells. Thus strategies to boost LDHA-mediated production of L-2HG or exogenous supplementation of L-2HG could be beneficial for tissue engineering or other stem cell-based therapeutics.

In some embodiments, the present disclosure systems or protocols that can be used to maintain or promote pluripotency or self-renewal of a cell, a tissue or an organism. In some embodiments, these systems or protocols can be used to maintain or promote or self-renewal of stem cells or progenitor cells. In some embodiments, these systems or protocols comprise modulating levels of L-2HG in the cells. In some embodiments, the present disclosure describes systems or protocols to modulate levels of L-2HG comprises contacting the cells with L-2HG. In some embodiments, the present disclosure describes systems or protocols to inhibit L-2-hydroxyglutarate dehydrogenase activity or expression. In some embodiments, the present disclosure describes systems or protocols to promote LDHA activity or expression. In some embodiments, the present disclosure describes systems or protocols to promote MDH1 or MDH2 activity or expression. In some embodiments, the present disclosure describes systems or protocols to deliver L-2HG to a cell. In some embodiments, the present disclosure describes systems or protocols to deplete alpha-ketoglutarate in a cell. In some embodiments, the systems or protocols that can be used to maintain or promote pluripotency or self-renewal of a cell or a tissue are applied in cell culture or tissue culture.

In some embodiments, the present disclosure describes systems or protocols for maintaining pluripotency and self-renewal of stem cells and progenitor cells in vivo in a subject by administering a composition comprising an agent that promote pluripotency and self-renewal of stem cells and progenitor cells.

Targeting L-2HG to Promote Differentiation of Stem Cells and Progenitor Cells.

In some embodiments, the present disclosure describes that accumulation of L-2HG leads to pluripotency of a cell. On the other hand, depletion of L-2HG or the inhibition of L-2HG through other mechanism promotes cell differentiation. In some embodiments, the present disclosure describes systems or protocols for promoting stem cell differentiation. In some embodiments, these systems or protocols comprise contacting a stem cell or a progenitor cell with an effective amount of an inhibitor of LDHA. In some embodiments, these systems or protocols comprise contacting a stem cell or a progenitor cell with an effective amount of an activator of L-2-hydroxyglutarate dehydrogenase. In some embodiments, the cell is a cancer stem cell.

The systems or protocols for maintaining pluripotence and/or self-renewing characteristics, or those for promoting cell differentiation, of the present invention are suitable for any stem cell or progenitor cell. As an illustrative example, any pluripotent human ESC or a respective cell line may be used in the respective method. Means of deriving a population of such cells are well established in the art (cf. e.g. Thomson, J. A. et al. [1998] Science 282, 1145-1147 or Cowan, C A. et al. [2004] JV. Engl. J. Med. 350, 1353-1356). Where the method is intended to be used for a progenitor cell, any progenitor cell may be used in this method of the invention. Examples of suitable progenitor cells include, but are not limited to, neuronal progenitor cells, endothelial progenitor cell, erythroid progenitor cells, cardiac progenitor cells, oligodendrocyte progenitor cells, retinal progenitor cells, or hematopoietic progenitor cells. Methods of obtaining progenitor cells are well known in the art. As two illustrative examples, a method of obtaining megakaryocyte progenitor cells has been disclosed in US patent application 2005/0176142 and a method of obtaining mouse liver progenitor cell lines has been described by Li et al. ((2005) Stem Cell Express, doi:10.1634/stemcells.2005-0108).

In some embodiments the selected L-2HG regulating genes (e.g., LDHA, MDH1/2, or L-2HG dehydrogenase), or a functional fragment thereof, are endogenously expressed in amounts that are sufficient for the performance of the present method of the invention. In other embodiments, the L-2HG regulating genes, or a functional fragment thereof, may be introduced into the cell by means of one or more recombinant vectors that include the genes encoding the desired transcription factors.

In other embodiments the present disclosure further includes contacting the respective cell with an agent that modulates L-2HG metabolism as described previously. In some embodiments, the agent is L-2HG. In some embodiments, the agent is α-KG.

The invention will be more fully understood by reference to the following examples. They should not, however, be construed as limiting the scope of the invention.

All literature citations in the present disclosure are incorporated by reference.

EXAMPLES

The following examples are provided for illustration and are not in any way to limit the scope of the invention.

Example 1: L-2-Hydroxglutarate Accumulates in Hypoxic Cells

Background:

The potential impact that specific metabolites can exert on cell responsiveness was exemplified by the identification of recurrent somatic mutations in isocitrate dehydrogenase 1 and 2 (IDH1/2) in a variety of human cancers (Amary et al., 2011; Borger et al., 2012; Cairns et al., 2012; Ley et al., 2008; Parsons et al., 2008; Patel et al., 2012; Yan et al., 2009). IDH1/2 are NADP$^+$-dependent enzymes that normally catalyze oxidative decarboxylation of isocitrate to α-ketoglutarate (α-KG) (Ward and Thompson, 2012).

Cancer-associated mutations in IDH1/2 result in a loss of wild type enzymatic activity with concomitant gain-of-function activity enabling conversion of α-KG to D-2-hydroxyglutarate (D-2HG) (Dang et al., 2009; Gross et al., 2010; Ward et al., 2010). D-2HG has been proposed to function as an 'oncometabolite' via its ability to inhibit a number of α-KG-dependent enzymes, including Jumonji histone lysine demethylases (Chowdhury et al., 2011; Figueroa et al., 2010; Lu et al., 2012; Xu et al., 2011). In particular, D-2HG-mediated inhibition of epigenetic modifying enzymes promotes repressive chromatin structure that impairs expression of genes required for normal differentiation in response to inductive growth factors/cytokines (Chen et al., 2013; Figueroa et al., 2010; Kats et al., 2014; Losman et al., 2013; Sasaki et al., 2012). Indeed, small-molecule inhibitors of IDH1/2-mutant enzymes can block D-2HG production, reverse repressive chromatin marks, and restore growth factor/cytokine-induced cellular differentiation (Rohle et al., 2013; Wang et al., 2013).

Of note, 2HG is a chiral molecule that can exist in either the D-(R)- or L-(S)-enantiomeric conformation (Linster et al., 2013). While IDH1/2 mutants exclusively produce D-2HG, biochemical evidence indicates that L-2HG can potently inhibit many α-KG-dependent enzymes, including epigenetic modifiers (Chowdhury et al., 2011; Koivunen et al., 2012; Xu et al., 2011).

Normal cells without IDH1/2 mutations produce small quantities of both D- and L-2HG via metabolic pathways that remain poorly understood (Linster et al., 2013). The evolutionarily conserved D- and L-2-hydroxyglutarate dehydrogenases (D2HGDH and L2HGDH) prevent accumulation of D- and L-2HG, respectively, by catalyzing their conversion back to α-KG (Achouri et al., 2004; Rzem et al., 2004). Homozygous germline loss-of-function mutations of D2HGDH or L2HGDH result in 2HG acidurias, disorders characterized by systemic elevation of D- or L-2HG (Kranendijk et al., 2012; Rzem et al., 2004; Struys et al., 2005). Patients with 2HG acidurias suffer from significant developmental abnormalities resulting in premature death (Kranendijk et al., 2012). Systemic elevations of L-2HG arising from inherited mutations of L2HGDH have been associated with brain tumors (Haliloglu et al., 2008; Moroni et al., 2004). Likewise, the recent identification of recurrent L2HGDH loss in kidney cancer alternatively or additionally supports a potential oncogenic role for deregulated L-2HG (Shim et al., 2014).

The 2HG acidurias demonstrate that physiologic D- and L-2HG levels must be tightly regulated by D2HGDH and L2HGDH in order to prevent 2HG-mediated pathology (Kranendijk et al., 2012). These findings raised the possibility that controlled physiologic production of D- or L-2HG might modulate specific cellular functions.

The foregoing observations provide evidence of the continuing need for the role of 2HG, especially the understudied L-2HG in stress-induced metabolism such as under conditions of hypoxia.

Materials and Methods:

Cell Culture: Adherent cell lines SF188, HEK293T, SH-SY5Y, and SV40-immortalized MEFs were maintained in high glucose DMEM, while hematopoietic cell lines 32D and FL5.12 were maintained in RMPI, with 10% FBS, glucose 25 mM, glutamine 4 mM, penicillin 100 units/ml, and streptomycin 100 microgram/ml and split every 2-3 days before reaching confluency. For hypoxia experiments, cells were cultured in a hypoxia chamber (Coy) at 0.5% oxygen for 24 to 48 hr prior to harvest. For siRNA experiments, SF188 or HEK293T cells were reverse-transfected with siRNA mixed with Lipofectamine RNAiMAX (Life Technologies) in Opti-MEM® Reduced Serum Medium (Life Technologies) as described by the manufacturer. L2HGDH cDNA was cloned by standard methods into the pCDH-CMV-MCS-EF1-Puro vector (pCDH) (System Biosciences). For generating SF188 cell lines with stable expression of shRNAs (PLKO.1), empty vector (pCDH), or L2HGDH (pCDH), supernatant from 293T cells transfected with helper virus and plasmids was collected after 72 hr, filtered and applied to SF188 parental cells overnight. Puromycin-resistant cells were selected by continuous culture puromycin 1 μg/ml.

shRNA experiments: The following TRC version 1 shRNAs in PLKO.1 vector (Sigma) were used: shL2HGDH-1 (L1)=clone ID: NM_024884.1-1113s1c1, sequence: CCGGCCACAGATGTTATGGATATAACTCGAGT-TATATCCATAACATCTGTGGTTTTT G (SEQ ID NO. 1); shL2HGDH-2 (L2)=clone ID: NM_024884.1-1370s1c1, sequence: CCGGCGCATTCTTCATGTGAGAAATCT-CGAGATTTCTCACATGAAGAATGCGTTTTT G (SEQ ID NO. 2); shL2HGDH-3 (L3)=clone ID: NM_024884.1-1217s1c1, sequence: CCGGGCAACAGTGAAGTATCTT-CAACTCGAGTTGAAGATACTTCACTGTTGCTTTTT G (SEQ ID NO. 3); shL2GHDH-4 (L4)=clone ID: NM_024884.1-674s1c1, sequence: CCGGGCTTTGTCAT-TTGCCCAGGATCTCGAGATCCTGGGCAAATGAC-AAAGCTTTTT G (SEQ ID NO. 4); shD2HGDH-2 (D2)= clone ID: NM_152783.2-630s1c1, sequence: CCGGGC-GTGTCTGGAATTCTGGTTTCTCGAGAAACCAGAAT-TCCAGACACGCTTTTT G (SEQ ID NO. 5); shD2HGDH-3 (D3)=clone ID: NM_152783.2-1270s1c1, sequence: CCGGCGACCAGAGGAAAGTCAAGATC-TCGAGATCTTGACTTTCCTCTGGTCGTTTTT G (SEQ ID NO. 6); shD2HGDH-4 (D4)=clone ID: NM_152783.2-319s1c1, sequence: CCGGGCCGTTCTCCACGGTGTC-TAACTCGAGTTAGACACCGTGGAGAACGGCTTTTT G (SEQ ID NO. 7); shD2HGDH-5 (D5)=clone ID: NM_152783.2-1066s1c1, sequence: CCGGCCTGTCTG-CATTCGAGTTCATCTCGAGATGAACTCGAATGCA-GACAGGTTTTT G (SEQ ID NO. 8).

Metabolite Extraction and GC-MS Analysis:

Metabolites were extracted with 1 mL ice-cold 80% methanol supplemented with 2 micromolar deuterated 2-hydroxyglutarate (D-2-hydroxyglutaric-2,3,3,4,4-d5 acid; deuterated-D-2HG) as an internal standard. After overnight incubation at −80° C., lysates were harvested, sonicated, then centrifuged at 21,000 g for 20 minutes at 4° C. to remove protein. Extracts were dried in an evaporator (Genevac EZ-2 Elite) and resuspended by incubation at 30° C. for 90 min in 50 microliters of methoxyamine hydrochloride 40 mg/mL in pyridine. Metabolites were alternatively or additionally derivatized by addition of 80 microliters of MSTFA+1% TCMS (Thermo Scientific) and 70 microliters of ethyl acetate (Sigma) and incubated at 37° C. for 30 min. Samples were analyzed using an Agilent 7890A GC coupled to Agilent 5975C mass selective detector. The GC was operated in splitless mode with constant helium gas flow at 1 mL/min. 1 microliter of derivatized metabolites was injected onto an HP-5MS column and the GC oven temperature ramped from 60° C. to 290° C. over 25 minutes. Peaks representing compounds of interest were extracted and integrated using MassHunter software (Agilent Technologies) and then normalized to both the internal standard (deuterated-D-2HG) peak area and protein content. Ions used for quantification of metabolite levels were 2HG m/z 247 and deuterated-2HG m/z 252. Peaks were manually inspected and verified relative to known spectra for each metabolite.

Chiral Derivatization:

In some experiments, cells were harvested in 80% methanol without internal standard. Methanol-extracted metabolites were dried in an evaporator (Genevac EZ-2 Elite), resuspended in water, run over AG 1-X8 anion exchange columns (Bio-Rad), eluted by 3N HCl, divided into 4 fractions, spiked with D-(R)-2HG or L-(S)-2HG standards (Sigma) or left unspiked, dried in an evaporator, sequentially derivatived with R(−)-2-butantol (Sigma) then acetic anhydride (Sigma) with heating to 95° C., dried under nitrogen flow, resuspended in ethyl acetate and analyzed by GC-MS as above. 2HG was identified as m/z 173. Chiral derivatization by this method allows for separation of L-2HG and D-2HG enantiomers by gas chromatography with L-2HG eluting at a shorter retention time than D-2HG.

Results:

Somatic mutations in isocitrate dehydrogenase 1 or 2 (IDH1/2) contribute to the pathogenesis of cancer via production of the 'oncometabolite' D-2-hydroxyglutarate (D-2HG). Elevated D-2HG can block differentiation of malignant cells by functioning as a competitive inhibitor of alpha-ketoglutarate (α-KG)-dependent enzymes, including Jumonji family histone lysine demethylases. 2HG is a chiral molecule that can exist in either the D- or L-enantiomer. Although cancer-associated IDH1/2 mutations exclusively produce D-2HG, biochemical studies have demonstrated that L-2HG alternatively or additionally functions as a potent inhibitor of α-KG-dependent enzymes.

Previous reports indicated that some cell types exhibit increased total 2HG levels under conditions of oxygen limitation (Albers et al., 1998; Wise et al., 2011). Indeed, the inventors identified a generalizable phenomenon wherein mammalian cells accumulate 2HG in response to hypoxia (FIG. 1A). The inventors used gas chromatography-mass spectrometry (GC-MS) to measure intracellular 2HG in IDH1/2-wildtype cell lines cultured in normoxia (21% oxygen) versus hypoxia (0.5% oxygen). In all cases, the inventors observed a substantial increase of 2HG in hypoxia, ranging from 5 to 25 fold depending on the type of cell (FIG. 1A). Importantly, standard methods for measuring metabolites by GC-MS do not distinguish enantiomeric species, thus total 2HG measured in these assays includes both D- and L-2HG.

The inventors next investigated the effects of manipulating D2HGDH or L2HGDH on intracellular 2HG levels. shRNAs targeting D2HGDH or L2HGDH were stably infected into the SF188 glioblastoma cell line, which has been used extensively to study metabolic pathways (DeBerardinis et al., 2007; Wise et al., 2008; Wise et al., 2011). Regardless of oxygen availability, ablation of D2HGDH had little effect on intracellular 2HG (FIG. 1B). However, ablation of L2HGDH substantially increased accumulation of 2HG in hypoxia, suggesting that L-2HG represents the major form of 2HG that accumulates in response to oxygen limitation (FIG. 1C). Similar results were obtained using HEK293T cells transfected with siRNAs targeting D2HGDH or L2HGDH.

Figure 6:
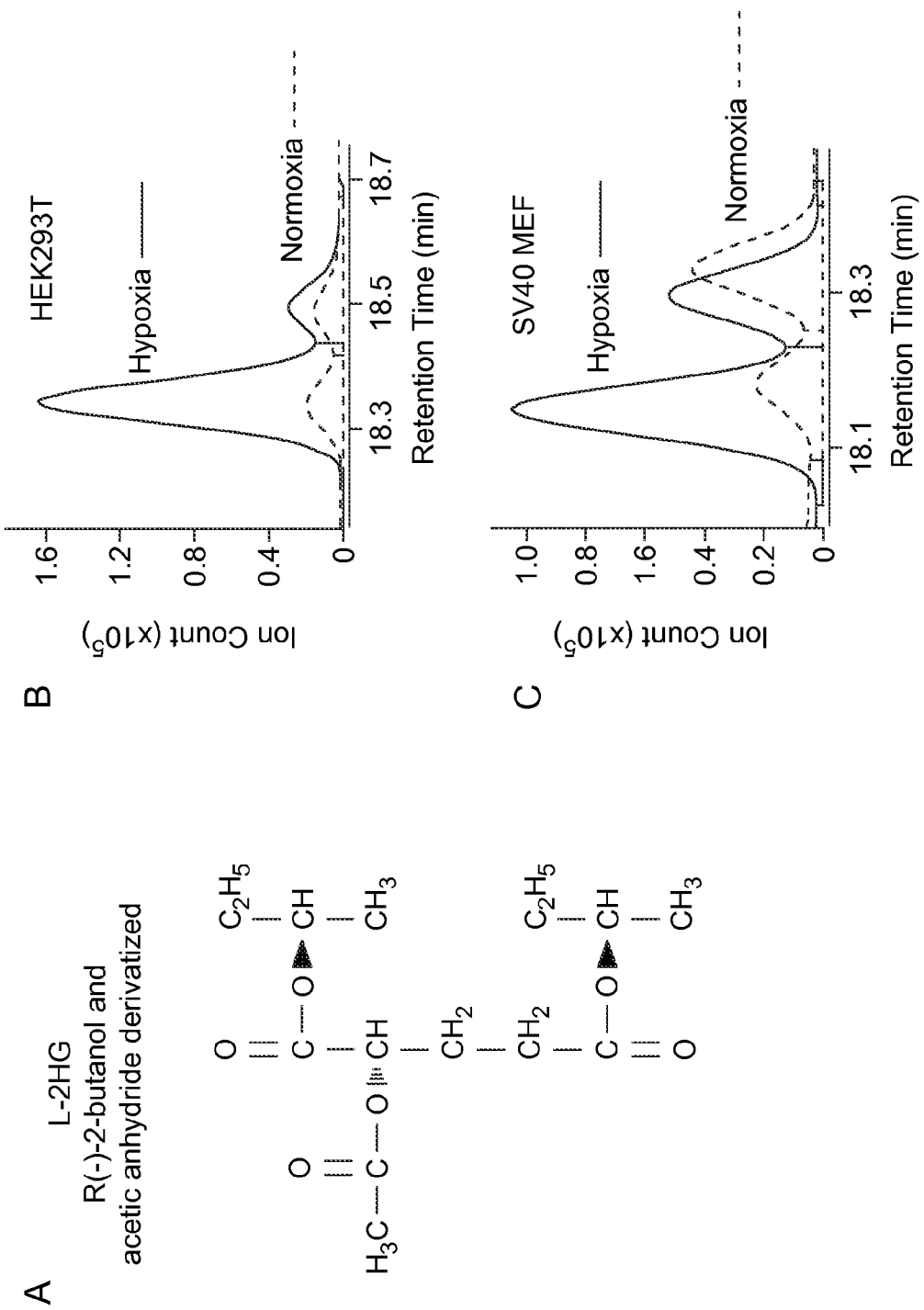
FIG. 6 depicts GC-MS histograms showing selective production of L-2HG in response to hypoxia. Panel (A) is a schematic showing L-2-hydroxyglutarate after sequential derivatization with R(−)-2-butanol and acetic anhydride (see Experimental Procedures for details). Panels in (B and C) are histograms from GC-MS. Metabolites from (B) HEK293T cells or (C) SV40-immortalized MEFs cultured in normoxia (21% O2) or hypoxia (0.5% O2) were subjected to chiral derivatization as in (A) to allow separation of 2HG enantiomers by GC-MS. L-2HG (left) elutes at a shorter retention time than D-2HG (right) as in demonstrated in FIG. 1D. Representative data from 1 of ≥2 independent experiments are shown.

In order to directly determine which enantiomer of 2HG accumulates in hypoxia, the inventors utilized a chiral derivatization procedure in which metabolites undergo sequential reaction with R(−)-2-butanol followed by acetic anhydride (FIG. 6A), thereby allowing D- and L-2HG to be distinguished by GC-MS (Ward et al., 2012; Ward et al., 2010). Prior to chiral derivatization, metabolite extracts from hypoxic SF188 cells were either left unmanipulated or spiked with commercially available standards of D-2HG, L-2HG, or a mixture of D- and L-2HG as references. This technique demonstrated that L-2HG was the major enantiomeric form of 2HG present in hypoxic cells (FIG. 1D). Chiral derivatization alternatively or additionally demonstrated that L-2HG was selectively produced in response to hypoxia in HEK293T cells and immortalized murine embryonic fibroblasts (MEF) (FIGS. 6B and 6C).

Example 2: Hypoxia-Induced L-2HG Originates from Glutamine-Derived α-KG

Materials and Methods:

Cell culture and GC-MS procedures are described in Example 1. For isotope tracing studies, media was changed at the indicated time before harvest using glucose- and glutamine-free DMEM media supplemented with $^{12}$C-glucose (Sigma) and $^{12}$C-glutamine (Gibco) or the $^{13}$C versions of each metabolite, [U-$^{13}$C]glucose or [U-$^{13}$C]glutamine (Cambridge Isotope Labs). Samples were harvested in 80% methanol without internal standard. Enrichment of $^{13}$C was assessed by quantifying the abundance of the 2HG ions, m/z 349-362. Correction for natural isotope abundance was performed using IsoCor software (Millard et al., 2012).

Figure 2:
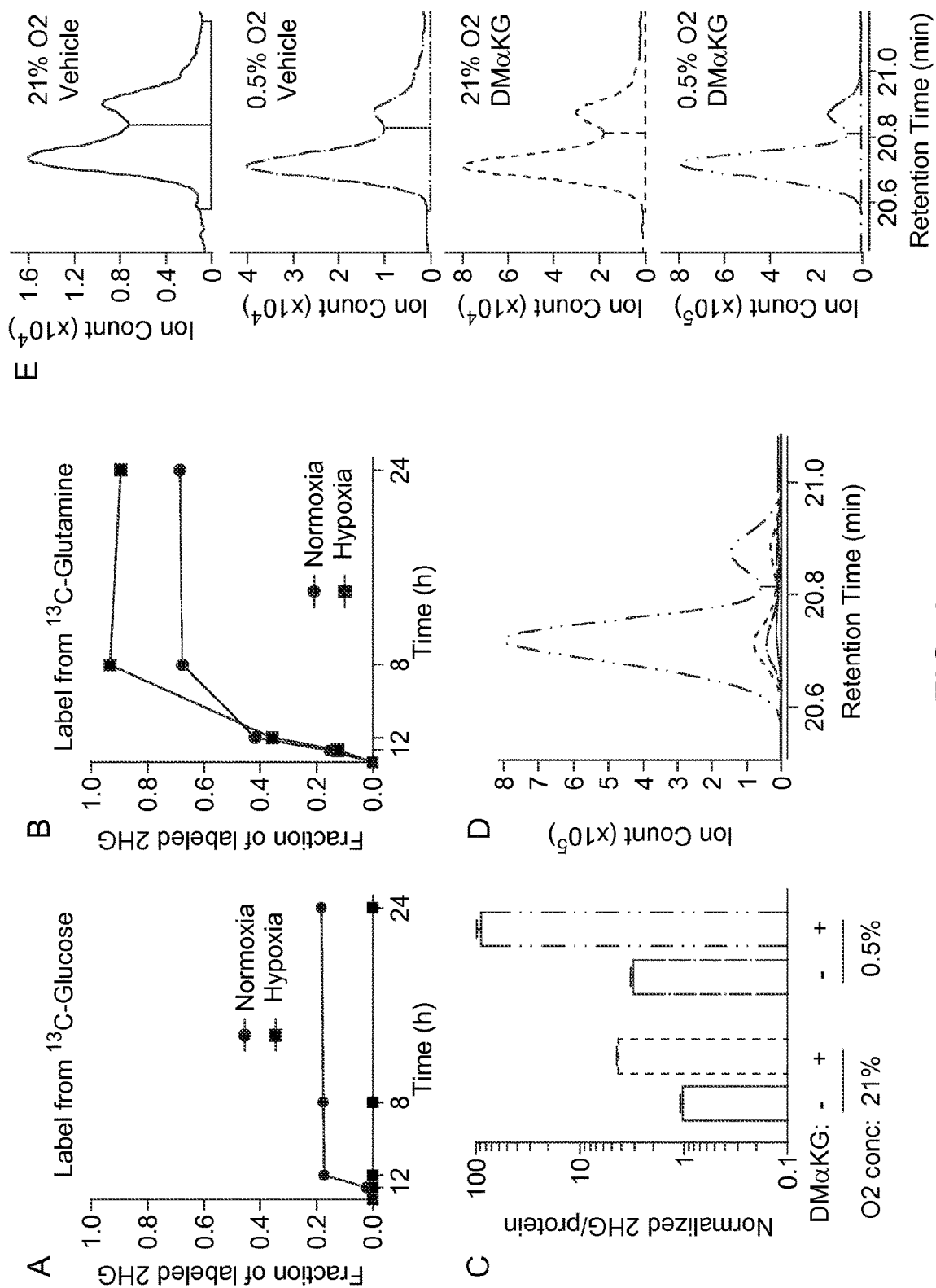
FIG. 2 depicts quantified results of GC-MS histograms showing that hypoxia-induced L-2HG originates from glutamine-derived α-ketoglutarate. Panels in (A and B) are line-drawings showing the fraction of intracellular 2HG labeled by $^{13}C$ at the indicated time. Isotope tracing was performed in SF188 cells cultured in medium containing either [U-$^{13}C$]glucose or [U-$^{13}C$]glutamine. A similar labeling pattern was observed in RCC4 and CS-1 cells (data not shown). Panels in (C) are bar graphs showing normalized 2HG. SF188 cells were cultured for 48 hr in 21% or 0.5% $O_2$ in the presence of vehicle (DMSO) or 5 mM dimethyl-α-KG. Total intracellular 2HG was assessed by GC-MS. Graph shows mean+/−SD of triplicate samples. Representative data from 1 of 3 independent experiments are shown. Panels in (D and E) are GC-MS histograms showing 2HG ions in different conditions. SF188 cells were cultured as in (C), then chiral derivatization of metabolites was performed to allow separation of 2HG enantiomers by GC-MS. Panels in (D) show an overlay of GC-MS histograms for 2HG on the same scale. Panels in (E) show individual GC-MS histograms for 2HG on different scales. The line style of the graphs for (D) and (E) is the same as shown in (C). L-2HG (left) elutes at a shorter retention time than D-2HG (right) as in (FIG. 1D). Representative data from 1 of 5 independent experiments are shown.

Results:

Glucose and glutamine represent two major nutrients which proliferating cells uptake and metabolize (Vander Heiden et al., 2009). The inventors performed metabolic flux analysis in SF188 cells supplemented with either [U-$^{13}$C] glucose or [U-$^{13}$C]glutamine in order to identify the source of the carbon backbone utilized to produce L-2HG in hypoxia (FIGS. 2A and 2B). In normoxia, the relatively small pool of total 2HG (FIG. 1A) was derived mostly from glutamine with a small contribution from glucose (FIGS. 2A and 2B). In contrast, the larger pool of hypoxia-induced L-2HG (FIGS. 1A and 1D) was derived exclusively from glutamine (FIGS. 2A and 2B).

Since cellular metabolism of glutamine generates α-ketoglutarate (Wise and Thompson, 2010), the inventors reasoned that hypoxia-induced L-2HG might arise from enzymatic reduction of glutamine-derived α-KG. The inventors tested the effect of supplementing cells with a cell-permeable form of α-KG. Addition of cell-permeable dimethyl-α-KG to SF188 cells in normoxia resulted in a modest increase in intracellular 2HG, while in hypoxia there was a nearly 100-fold increase in 2HG (FIG. 2C), which was confirmed to be L-2HG by chiral derivatization (FIGS. 2D and 2E). In agreement with a previous study of cells from patients with L-2HG aciduria (Struys et al., 2007), these findings suggest that hypoxia-induced L-2HG arises from enzymatic reduction of glutamine-derived α-KG.

Discussion:

Nutrients and metabolites influence fundamental cellular processes (Kaelin and McKnight, 2013; Vander Heiden et al., 2009). For example, α-KG serves as an essential substrate for approximately 70 different enzymes involved in such diverse functions as demethylation of histones and DNA, regulation of HIF1α stability, and maturation of collagen (Losman and Kaelin, 2013). By coupling these enzymatic processes to α-KG availability, the metabolic fitness of the cell can be intimately linked to important cellular 'decisions' such as lineage differentiation and adaptation to environmental stressors. Inhibition of α-KG-dependent enzyme activity by the 'oncometabolite' D-2HG appears to represent the primary mechanism whereby oncogenic mutations in IDH1/2 disrupt normal cellular physiology (Kaelin and McKnight, 2013; Losman and Kaelin, 2013; Ward and Thompson, 2012). Similarly, children born with loss-of-function mutations in both parental alleles of either L2HGDH or D2HGDH accumulate L-2HG and D-2HG, respectively, resulting in severe developmental defects (Kranendijk et al., 2012; Rzem et al., 2004; Struys et al., 2005).

Example 3: Hypoxia-Induced L-2HG Results from Promiscuous Substrate Usage by LDHA Materials and Methods:

Cell culture and GC-MS procedures are described in Example 1.

Western Blotting:

Cell lysates were extracted in 1x RIPA buffer (Cell Signaling), sonicated, centrifuged at 14,000 g at 4° C., and supernatants were collected. For histone acid-extraction, cells were lysed in hypotonic lysis buffer (Amresco) for 1 hr. $H_2So_4$ was added to 0.2 N overnight at 4° C. with rotation, and supernatants were collected after centrifugation. Histones were precipitated in 33% TCA, washed with acetone, and resuspended in deionized water. Cleared cell lysates or histone preparations were normalized for total protein concentration. Samples were separated by SDS-PAGE, transferred to nitrocellulose membranes (Life Technologies), blocked in 5% milk prepared in Tris buffered saline with 0.1% Tween 20 (TBST), incubated with primary antibodies overnight at 4° C. then horseradish peroxidase (HRP)-conjugated secondary antibodies (GE Healthcare, NA931V and NA934V) for 1 hr the following day. After ECL application (Thermo Scientific), imaging was performed using the SRX-101A (Konica Minolta). For in vitro histone demethylase assays, bulk calf thymus histones (Sigma) were incubated with GST-tagged KDM4C (BPS Bioscience) in a reaction mixture containing Tris-HCl 50 mM, pH 8.0, protease inhibitors, α-KG 1 mM, FeSO4 100 micromolar, and ascorbic acid 2 micromolar. The reaction mixture was incubated at 37° C. for 4 hr in the absence or presence of various concentrations of L-2HG or D-2HG (Sigma). H3K9me3 levels were analyzed by Western blot with total histone H3 used as the loading control. Primary antibodies used included: anti-L2HGDH (Proteintech, 15707-1-AP), anti-D2HGDH (Proteintech, 13895-1-AP), anti-LDHA (Cell Signaling, 2012), anti-IDH1 (anti-IDH2 (Abcam, ab55271), anti-MDH1 (Abcam, ab55528), anti-MDH2 (Abcam, ab96193), anti-tubulin (Sigma, T9026), anti-S6 ribosomal protein (Cell Signaling, 2317), anti-HIF1α(BD Biosciences, 610959), anti-H3 (Cell Signaling, 4499), and anti-H3K9me3 (Active Motif, 39765).

siRNA Experiments:

The following siRNAs (Thermo Scientific) were used:

```
siIDH1-a = J-008294-10, target sequence:
GCAUAAUGUUGGCGUCAAA;         (SEQ ID NO. 9)

siIDH1-b = J-008294-11, target sequence:
GCUUGUGAGUGGAUGGGUA;         (SEQ ID NO. 10)

siIDH2-a = J-004013-09, target sequence:
GCAAGAACUAUGACGGAGA;         (SEQ ID NO. 11)

siIDH2-b = J-004013-12, target sequence:
GCGCCACUAUGCCGACAAA;         (SEQ ID NO. 12)

siMDH1-a = J-009264-10, target sequence:
GGGAGAAUUUGUCACGACU;         (SEQ ID NO. 13)

siMDH1-b = J-009264-12, target sequence:
AGGUUAUUGUUGUGGGUAA;         (SEQ ID NO. 14)

siMDH2-a = J-008439-10, target sequence:
GAUCUGAGCCACAUCGAGA;         (SEQ ID NO. 15)

siMDH2-b = J-008439-12, target sequence:
CGCCUGACCCUCUAUGAUA;         (SEQ ID NO. 16)

siLDHA-a = J-008201-05, target sequence:
GGAGAAAGCCGUCUUAAUU;         (SEQ ID NO. 17)

siLDHA-b = J-008201-06, target sequence:
GGCAAAGACUAUAAUGUAA;         (SEQ ID NO. 18)

siLDHA-c = J-008201-07, target sequence:
UAAGGGUCUUUACGGAAUA;         (SEQ ID NO. 19)

siLDHA-d = J-008201-08, target sequence:
AAAGUCUUCUGAUGUCAUA          (SEQ ID NO. 20)
```

Figure 3:
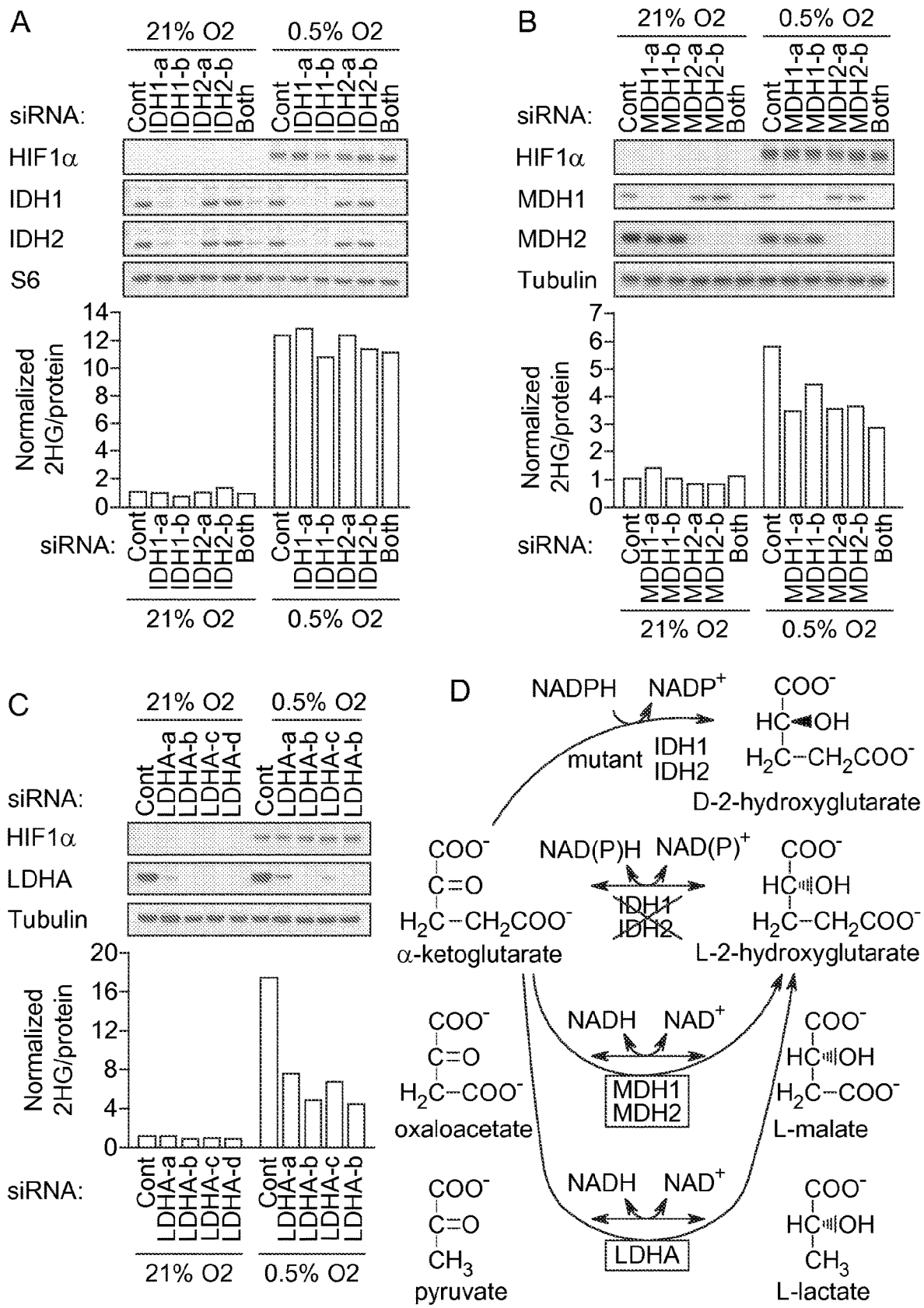
FIG. 3 depicts western blot images showing that hypoxia-induced L-2HG arises via promiscuous substrate usage by LDHA. Panels in (A, B, C) are west blot images and quantification of various proteins as indicated after siRNA experiments. SF188 cells were transfected with siRNAs targeting (A) IDH1 (IDH1-a, -b) or IDH2 (IDH2-a, -b), (B) MDH1 (MDH1-a, -b) or MDH2 (MDH2-a, -b), or (C) LDHA (LDHA-a, -b, -c, -d). 48 hr after transfection, cells were transferred to 21% or 0.5% $O_2$ for an additional 24 to 48 hr, followed by measurement of intracellular 2HG. Western blot confirms target knockdown efficiency and shows hypoxia-induced expression of HIF1α. Expression of either S6 protein or α-tubulin is shown as loading controls. For each panel, representative data from 1 of 3 independent experiments are shown. See also FIG. 7. Panel (D) is a schematic drawing summarizing enzymatic sources of hypoxia-induced L-2HG.
Figure 7:
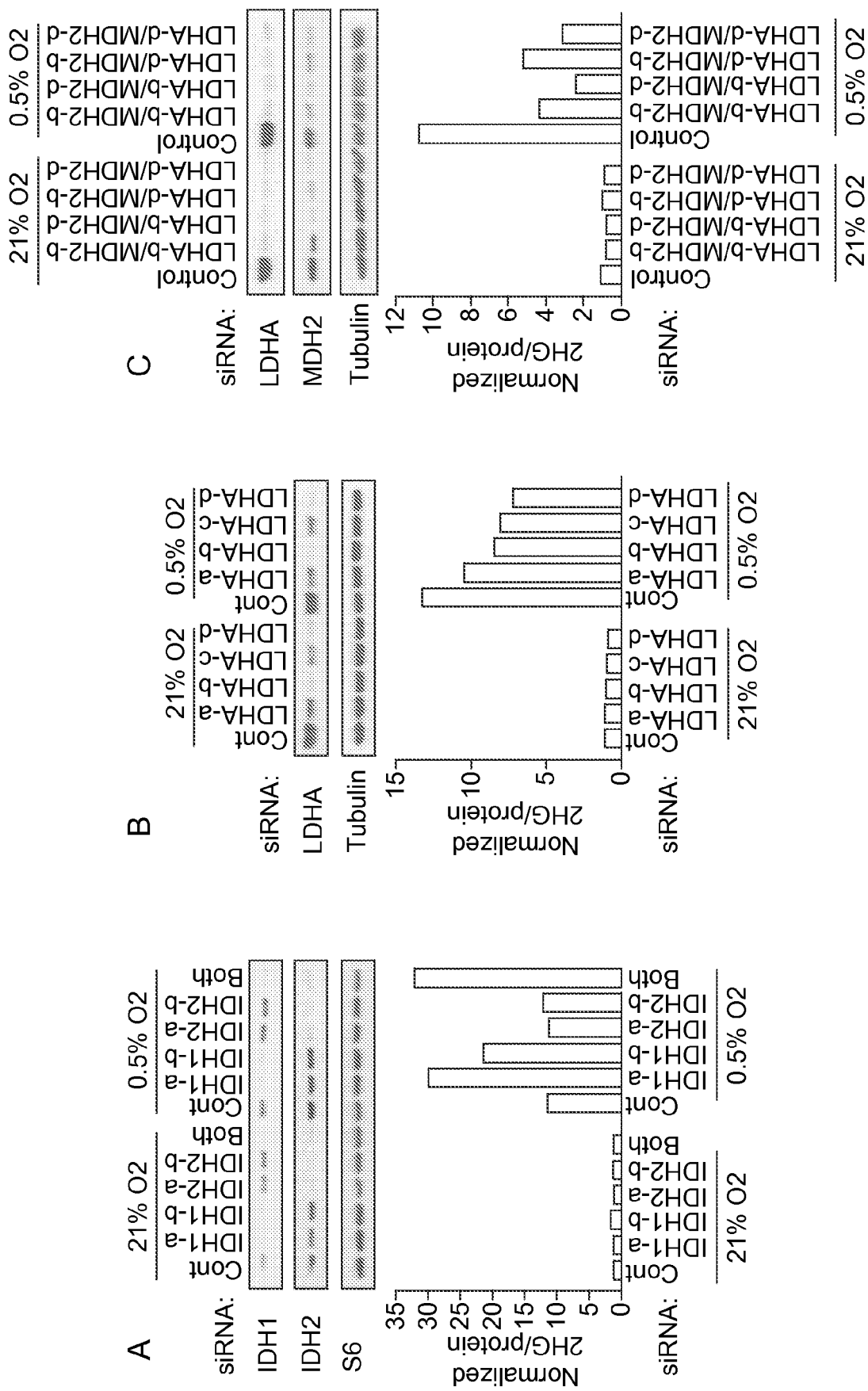
FIG. 7 depicts western blots images showing the enzymatic sources of hypoxia-induced L-2HG. Top panels are western blot images of proteins as indicated on the left side of the panels under conditions indicated, and bottom panels are quantification of the western blots. HEK293T cells were transfected with siRNAs targeting (A) IDH1 (IDH1-a, -b) or IDH2 (IDH2-a, -b), (B) LDHA (LDHA-a, -b, -c, -d), or (C) both LDHA (LDHA-b, -d) and MDH2 (MDH2-a, -b). 48 hr after transfection, cells were transferred to 21% or 0.5% O2 for an additional 24 to 48 hr, followed by measurement of intracellular 2HG. Western blot confirms target knockdown efficiency with expression of either S6 protein or α-tubulin shown as loading controls. For each panel, representative data from 1 of ≥2 independent experiments are shown.

Results:

In order to determine the enzymatic source(s) of hypoxia-induced L-2HG, the inventors ablated candidate metabolic enzymes by siRNA (FIG. 3). Knockdown of IDH1 or IDH2 did not impair production of L-2HG in hypoxic SF188 cells (FIG. 3A). Likewise, HEK293T cells subjected to siRNA-mediated ablation of IDH1, IDH2, or both IDH1 and IDH2 together, exhibited no dependence on these enzymes for production of L-2HG in response to hypoxia (FIG. 7A). These observations are consistent with the fact that the α-hydroxyl group in naturally occurring isocitrate (analogous to the α-hydroxyl group of 2HG) always exists in the D-(R)-enantiomeric conformation due to the stereochemistry of enzymatic reactions catalyzed by isocitrate dehydrogenases (Patterson et al., 1962; Sprecher et al., 1964). Thus, IDH1/2 enzymes are likely incapable of reducing α-KG to L-2-hydroxyglutarate due to steric constraints on substrate binding.

Metabolic enzymes can exhibit 'promiscuous' catalytic activities (Linster et al., 2013), and previous cellular fractionation studies implicated cytosolic malate dehydrogenase 1 (MDH1) and mitochondrial malate dehydrogenase 2 (MDH2) as possible enzymatic sources of L-2HG (Rzem et al., 2007). The inventors tested the requirement for metabolic enzymes whose primary catalytic activities involve reduction of α-ketoacid substrates to L-hydroxyl acids with structural similarities to α-KG and L-2HG, respectively (FIG. 3D). In SF188 cells, the inventors identified a partial contribution from MDH1 and MDH2 to hypoxia-induced L-2HG (FIG. 3B). Strikingly, however, lactate dehydrogenase A (LDHA) was identified as the major enzyme required for hypoxia-induced L-2HG in SF188 cells (FIG. 3C). These observations were confirmed in HEK293T cells, where combined ablation of LDHA and MDH2 also resulted in a near total abrogation of hypoxia-induced L-2HG (Figures S7B and S7C). Collectively, these findings suggest that hypoxic cells can produce L-2HG from reduction of glutamine-derived α-KG in the cytoplasm via promiscuous substrate usage by LDHA, with a smaller contribution from cytosolic MDH1 and mitochondrial MDH2 (FIG. 3D).

Abrogation of hypoxia-induced L-2HG had no major effects on HIF1α protein levels (FIGS. 3B and 3C). Previous reports demonstrated that L-2HG can stabilize HIF1α in normoxia via L-2HG-mediated inhibition of the EGLN family of α-KG-dependent prolyl hydroxylases that mark HIF1α for proteasomal degradation (Chowdhury et al., 2011; Koivunen et al., 2012; Losman et al., 2013). Consistent with these observations, the inventors noted minor increases in HIF1α protein levels in hypoxic cells subjected to ablation of L2HGDH (with consequent enhancement of hypoxia-induced L-2HG) (FIG. 1C). However, it appears that reduced oxygen availability (0.5%) is sufficient to impair the activity of EGLN prolyl hydroxylases even in the absence of elevations in L-2HG (FIG. 3C).

Discussion:

In contrast to the intensive research efforts focused on elucidating the role of D-2HG in the molecular pathogenesis of IDH1/2-mutant malignancies, less attention has been paid to the potential roles for controlled production and elimination of D-2HG and L-2HG in normal cellular physiology (Kranendijk et al., 2012). The findings presented here identify L-2HG induction as a novel cellular metabolic response to the environmental stress imposed by hypoxia. Under conditions of oxygen limitation, cells accumulate TCA cycle intermediates as well as cytosolic and mitochondrial reducing equivalents in the form of NADH (Bensaad and Harris, 2014; Metallo et al., 2012; Semenza, 2013; Wise et al., 2011; Zhdanov et al., 2014), which will favor the enzymatic reduction of α-KG to produce the L-2HG documented here. Production of L-2HG in hypoxia occurs independently of IDH1/2, instead arising via promiscuous enzymatic reduction of α-KG primarily by LDHA. Hypoxia-induced L-2HG represents a molecular mechanism whereby cells might repress α-KG-dependent processes (e.g. demethylation of H3K9me3) when faced with limited oxygen availability. Alternatively or additionally, L-2HG can suppress α-KG-dependent reversal of hypoxic adaptation. α-KG is required to initiate HIF1α clearance and to restore expression of genes silenced by histone methylation (Kaelin and Ratcliffe, 2008; Kooistra and Helin, 2012; Ozer and Bruick, 2007; Tausendschon et al., 2011). Thus, hypoxia-induced L-2HG represents a means through which cells can maintain repression of α-KG-dependent processes that might counteract hypoxic adaptation.

Alternative or promiscuous substrate usage is a well-described property of many metabolic enzymes, including lactate dehydrogenases (Linster et al., 2013; Meister, 1950; Schatz and Segal, 1969). The ability of LDHA to catalyze reduction of α-KG to L-2HG in hypoxia represents an example of alternative substrate usage that might mediate meaningful biologic effects. Production of L-2HG by LDHA represents a parsimonious mechanism wherein a single enzyme functions as both a mediator of anaerobic glycolysis and an initiator of a metabolic signaling pathway that transmits information about the cellular metabolic state to the nucleus. LDHA expression is upregulated in hypoxia by HIF1α (Hu et al., 2003) and subsequent LDHA-dependent conversion of αKG into L-2HG may provide a positive feedback loop to sustain hypoxic adaptation. Zhdanov et al. (2014) recently demonstrated that sustained nuclear HIF1α accumulation is dependent on ongoing glutamine metabolism during hypoxic adaptation. Consistent with this, the inventors find that hypoxia-induced accumulation of L-2HG is also glutamine dependent. These findings suggest a link between glutamine-dependent L-2HG production in hypoxia and sustained HIF1a induction.

The selective accumulation of L-2HG in hypoxia underscores the importance of distinguishing between 2HG enantiomeric species (Terunuma et al., 2014). L-2HG has been shown to function as a competitive inhibitor of the EGLN prolyl hydroxylases, suppressing their ability to initiate HIF1a degradation and terminate hypoxic adaptation. In contrast, D-2HG can act as a substrate for the EGLN prolyl hydroxylases to promote the hydroxylation and degradation of HIF1α, thus impeding hypoxic adaptation (Koivunen et al., 2012; Losman et al., 2013). Taken together, the present results favor a supportive role for hypoxia-induced L-2HG in reinforcing the HIF1α axis and maintaining cellular adaptation to hypoxia, properties not shared by D-2HG.

Example 4: The Active Site of LDHA can Accommodate Reduction of α-KG to L-2HG

Materials and Methods:

Cell culture and GC-MS procedures are described in Example 1.

Molecular Docking of Putative LDHA Substrates:

Docking of putative substrate and product molecules was performed using Glide in Maestro 2014-3 (Friesner et al., 2004; Friesner et al., 2006; Halgren et al., 2004; Schrödinger, 2014). Ligands were docked into chain A of PDB structure 1I10 after removing crystallographic waters and ligands except for NADH (Read et al., 2001). Missing side chains and loops were automatically rebuilt using Prime (Jacobson et al., 2002; Jacobson et al., 2004). PROPKA was used to assign protonation states compatible with a pH of 7 (Olsson et al., 2011; Sondergaard et al., 2011). Bond orders for NADH or NAD+ were manually verified to avoid misassignment by PROPKA. Restrained minimization was performed using OPLS2005 (Banks et al., 2005). Oxamate was used as a reference ligand to define the binding site, after adding fictitious atoms to ensure minimum atom requirement for binding site definition was met. Hydroxyl and thiol groups were allowed to rotate during grid generation. Pyruvate and α-ketoglutarate were docked in the presence of crystallographic NADH. Lactate and L-2-hydroxyglutarate were docked in the presence of NAD+ modeled from crystallographic NADH by alteration of bond orders. Carboxylic acid moieties of the ligands were fully deprotonated. Docking was performed using Extra Precision Glide with flexible ligands (Friesner et al., 2004; Friesner et al., 2006; Halgren et al., 2004). Docking poses were minimized post-docking. The resulting conformations were clustered within a 1 angstrom RMSD cutoff. This resulted in a single representative pose for each of the docked ligands. All steps utilized default parameters unless otherwise noted. Poses and predicted hydrogen bonds were visualized using PyMOL (The PyMOL Molecular Graphics System, Version 1.7.0.0 Schrödinger, LLC).

Figure 4:
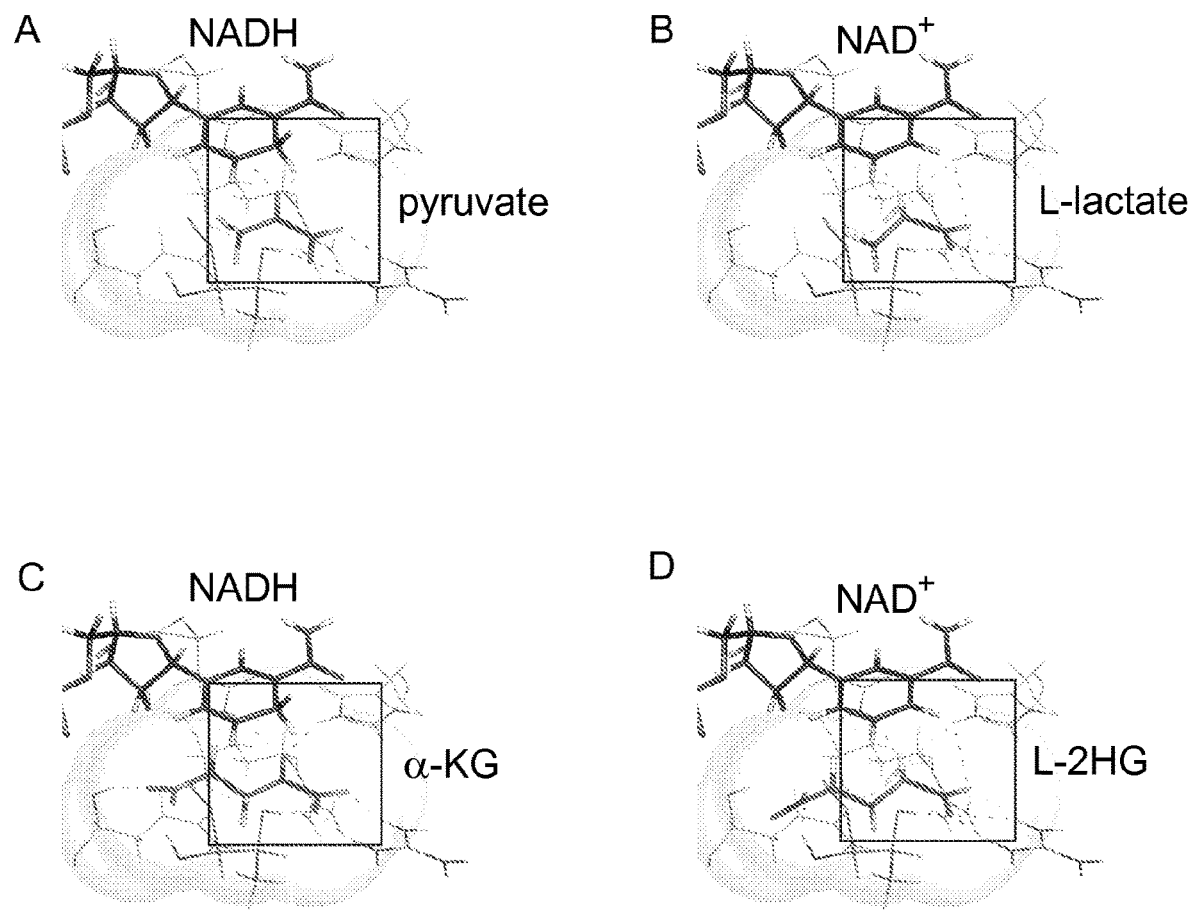
FIG. 4 depicts structural modeling renderings showing that the active site of LDHA can sterically accommodate binding of α-KG in a geometry amenable for reduction to L-2HG. Panels in (A and C) are structural models of docked poses of pyruvate and α-KG to the active site of LDHA with NADH. Panels in (B and D) are structural models of docked poses of L-lactate and L-2HG to the active site of LDHA with NAD+. The shadowed cloud is a representation of predicted empty space within the substrate-binding pocket. Predicted hydrogen bonds are shown in blue. Residues shown as lines are Arg168 (thin gray lines on top right corners of panels), Thr247 (thick gray lines on top left corners of the panels), His192 (thin gray lines in bottom middle), Arg105 (light gray lines in the middle in the background), Asn137 (thin gray lines on top middle), and Gln99 (thick gray lines on top middle between light gray and black). Docking utilized PDB accession code 1I10 (Read et al., 2001). The rectangular boxes highlight the spatial configurations of the carboxylic acid head group and adjacent carbonyl group of each substrate in relation to the hydride group of NADH, which constrains the reductive reactions to produce the L-(S)-enantiomers of the corresponding α-hydroxyl acids.

Results:

To better understand how LDHA might catalyze reduction of α-KG to L-2HG, the inventors performed molecular docking of putative substrates to the active site of LDHA. The resulting docking poses demonstrated that pyruvate was spatially coordinated by hydrogen bonding to the carboxylic acid head group and adjacent carbonyl group (FIG. 4A). Nucleophilic attack of pyruvate's carbonyl carbon by the hydride group from NADH is spatially restricted such that the reductive reaction exclusively produces the L-(S)-enantiomer of lactate (FIG. 4B). Likewise, molecular docking of α-ketoglutarate showed that it could favorably adopt a similar spatial coordination to pyruvate via identical hydrogen bonding to the carboxylic acid head group and adjacent carbonyl group (FIG. 4C). Importantly, there was considerable steric space available in the substrate-binding pocket of LDHA to accommodate the longer tail of α-ketoglutarate without unfavorable steric interactions (FIG. 4C). Analogous to the reduction of pyruvate to L-lactate, nucleophilic attack of the carbonyl carbon of α-KG was spatially constrained such that L-2-hydroxyglutarate would be the exclusive end product of the reductive reaction (FIG. 4D). Taken together, these findings alternatively or additionally support the genetic data identifying LDHA as a major enzymatic source of hypoxia-induced L-2HG (FIGS. 3C, 7B, 7C).

Example 5: L-2HG Mediates Epigenetic Changes in Response to Hypoxia

Materials and Methods:
Human Glioblastoma Specimens:
Human glioblastoma biopsy specimens were obtained from the University of Pennsylvania following approval from the institutional review board. All cases were de-identified prior to analysis and were contained in a previously well-characterized tissue microarray (Venneti et al., 2013a).

Immunohistochemical Analysis:
Immunohistochemical studies and quantification were performed as previously described (Venneti et al., 2013b). In brief, immunostaining was performed using the Discovery XT processor (Ventana Medical Systems). Tissue sections were blocked for 30 min in 10% normal goat serum in 2% BSA in PBS. Sections were incubated for 5 hr with 10 microgram/ml of the mouse monoclonal anti-HIF1α(Alexis Biochem, ALX-210-069) or 0.1 microgram/ml of the rabbit polyclonal anti-H3K9me3 antibodies (Abcam, ab8898). Tissue sections were then incubated for 60 min with biotinylated goat anti-mouse or anti-rabbit IgG (Vector labs, PK6102 and PK6101) at 1:200 dilution. Blocker D, Streptavidin-HRP and DAB detection kit (Ventana Medical Systems) were used according to the manufacturer instructions.

For automated scoring, slides were scanned using a Pannoramic Flash 250 scanner (Perkin Elmer, Waltham Mass.) and viewed through the Pannormaic viewer software program (3D Histech, Waltham Mass.). An individual blinded to the experimental design captured JPEG images at 10× magnification. Quantification of immunostaining on each JPEG was conducted using an automated analysis program with Matlab's image processing toolbox based on previously described methodology (Venneti et al., 2013b). The algorithm used color segmentation with RGB color differentiation, K-Means Clustering and background-foreground separation with Otsu's thresholding. To arrive at a score the number of extracted pixels were multiplied by their average intensity for each core (represented as pixel units). The final score for a given case and marker was calculated by averaging the score of two cores (for each case) for a given marker.

Results:
Biochemically, both D-2HG and L-2HG have been reported to inhibit the Jumonji family histone lysine demethylase KDM4C, resulting in aberrant accumulation of trimethylated histone 3 lysine 9 (H3K9me3) and impairment of normal cellular differentiation (Chen et al., 2013; Chowdhury et al., 2011; Kats et al., 2014; Lu et al., 2012; Rohle et al., 2013; Sasaki et al., 2012). In glioblastomas, IDH1/2 mutation is associated with diffuse increases in H3K9me3 throughout the tumor, whereas H3K9me3 shows regional variations in tumors without IDH1/2 mutation (Venneti et al., 2013a).

Figure 5:
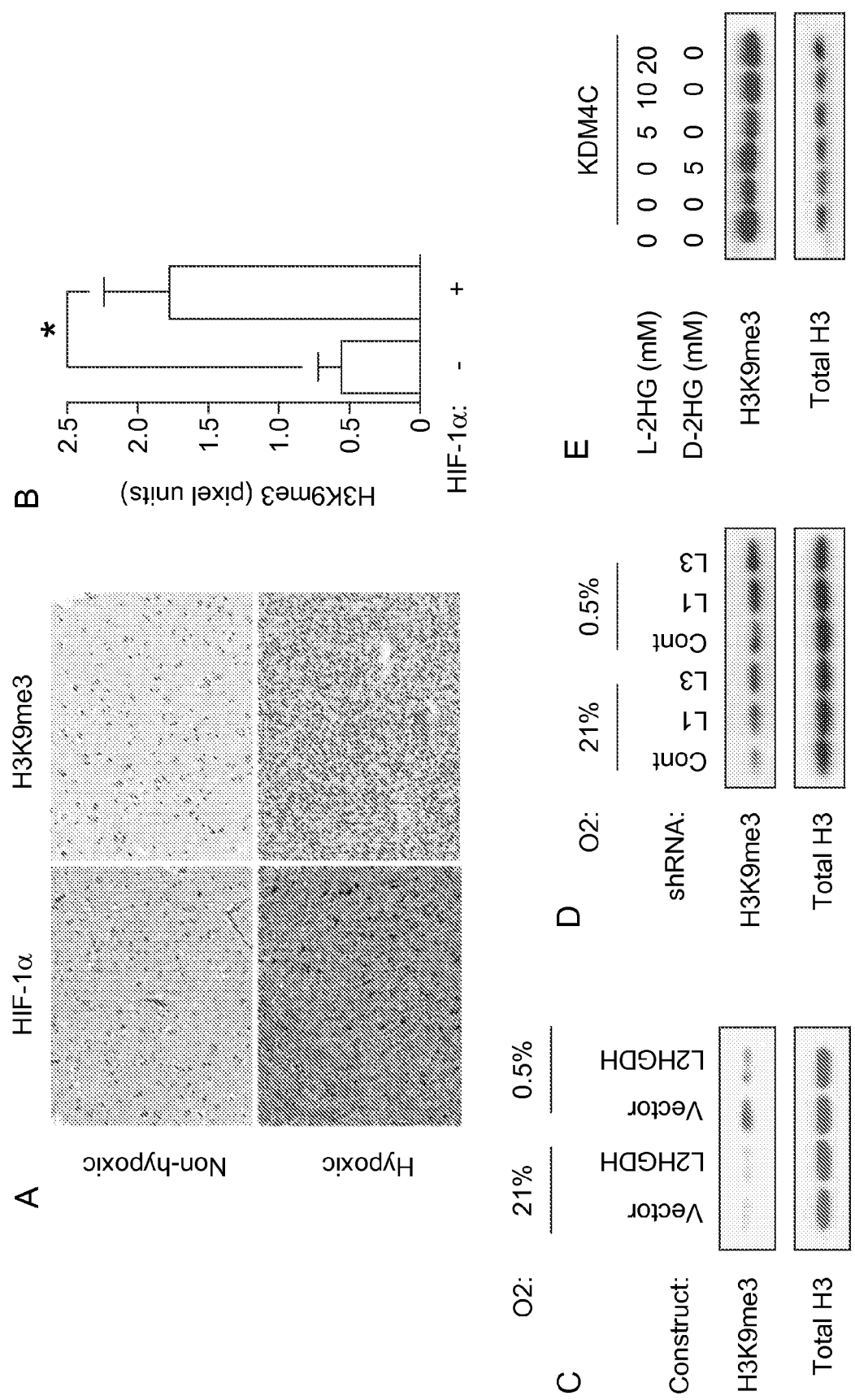
FIG. 5 depicts immunohistochemistry staining and western blot images showing that L-2HG enhances trimethylation of histone 3 lysine 9 in response to hypoxia. Panels in (A) are immunohistochemistry images of human glioblastomas specimens stained for proteins indicated. HIF1α expression and H3K9me3 levels were assessed by immunohistochemistry in human glioblastomas specimens with (n=26) or without (n=21) hypoxic regions captured in the biopsy. Panel (B) shows quantification of H3K9me3 staining intensity (pixel units) within biopsies not expressing (−) or expressing (+) HIF1α. Values represent mean+/−SD; *p=0.01 determined by unpaired two-tailed Student's t test. Panels in (C, D and E) are western blot images and quantified results of H3K9me3 under conditions indicated. SF188 glioblastoma cells stably infected with empty lentiviral vector (Vector) or lentiviral vector encoding L2HGDH were cultured for 48 hr in 21% or 0.5% $O_2$, followed by histone extraction and assessment of H3K9me3 by Western blot. (D) SF188 glioblastoma cells stably infected with lentiviruses expressing non-targeting shRNA (Cont) or shRNAs targeting L2HGDH (L1, L3) were cultured in 21% or 0.5% $O_2$, followed by histone extraction and assessment of H3K9me3 by Western blot. Panels in (E) Bulk histones were incubated with purified human KDM4C in a reaction mixture with α-KG (1 mM), as well as the indicated concentrations of L-2HG or D-2HG. H3K9me3 was assessed by Western blot with total H3 used as loading control. Panels in (C), (D), and (E) show representative data from 1 of 3 independent experiments.

The above results suggest that the variability in H3K9me3 staining in IDH1/2-wildtype glioblastomas might correlate with regions of hypoxia. To test this idea, the inventors determined the correlation between HIF1α expression and H3K9me3 by immunohistochemistry using 47 human glioblastoma samples wild type for IDH1/2 (FIG. 5A). HIF1α expression and H3K9me3 were highly statistically correlated in these samples (p=0.01) (FIG. 5B).

These observations suggested that hypoxia-induced L-2HG might mediate the enhancement of H3K9me3 observed in vascularly compromised regions of human glioblastoma. To test this hypothesis, the human glioblastoma cell line SF188 was stably infected with a lentivirus expressing L2HGDH or an empty lentiviral vector. SF188 glioblastoma cells infected with empty vector exhibited increased global levels of H3K9me3 in response to hypoxia (FIG. 5C), consistent with the findings from the primary glioblastoma specimens (FIGS. 5A and 5B). However, when hypoxia-induced L-2HG was abrogated by overexpression of L2HGDH, there was a substantial reduction in hypoxia-induced H3K9me3 (FIG. 5C). Conversely, ablation of L2HGDH (with consequent increase of hypoxia-induced L-2HG) resulted in increased H3K9me3 (FIG. 5D). A similar pattern, albeit less robust, was observed with H3K27me3 (data not shown).

The inventors performed in vitro histone demethylation assays to determine whether the effect on H3K9me3 might be mediated through direct inhibition of KDM4C by hypoxia-induced L-2HG. Addition of purified KDM4C to histone substrates resulted in demethylation of H3K9me3 that was sensitive to inhibition by L-2HG, in a dose dependent manner (FIG. 5D). These observations are consistent with prior reports demonstrating roughly comparable inhibition of KDM4C by L-2HG and D-2HG (Chowdhury et al., 2011; Lu et al., 2012). Thus, induction of L-2HG appears to enhance H3K9me3 in response to hypoxia.

Discussion:
In contrast to their disparate roles in regulating EGLN-dependent proline hydroxylation of HIF1α, both L-2HG and D-2HG function as inhibitors of histone demethylases (Chowdhury et al., 2011; Koivunen et al., 2012; Lu et al., 2012; Xu et al., 2011). Like oncogenic levels of D-2HG, hypoxia-induced levels of L-2HG result in enhanced repressive histone methylation. While the oncogenic production of D-2HG by IDH1/2 mutations leads to a cancer-promoting block to differentiation, hypoxia-induced L-2HG might function as a physiologic regulator of stem/progenitor cell differentiation. Hypoxia-induced L-2HG might account, at least in part, for the importance of both hypoxic niches and LDHA for maintaining the self-renewal of various stem cell populations (Nombela-Arrieta et al., 2013; Simon and Keith, 2008; Spencer et al., 2014; Suda et al., 2011; Wang et al., 2014; Xie et al., 2014). Specifically, normal stem cells residing in hypoxic niches may produce sufficient L-2HG to maintain the silencing of genes required for differentiation, thus maintaining a progenitor/stem cell fate. Consistent with this, Shim et al. (2014) have recently shown that loss of L2GHDH during cancer progression results in accumulation of L-2HG and alterations in repressive histone methylation similar to those observed here in response to hypoxia. Finally, our results studying biopsies from patients with glioblastomas suggest that hypoxic induction of L-2GH may contribute to the development of epigenetic heterogeneity in this tumor type. Whether these results apply to other tumor types will be the subject of future investigations.

The present Examples support the description included herein of a novel metabolic pathway whereby IDH1/2-wildtype cells selectively produce L-2HG via enzymatic reduction of α-KG during hypoxia. Hypoxia-induced L-2HG does not depend on either IDH1 or IDH2, but instead arises via promiscuous substrate usage by lactate dehydrogenase A (LDHA), with additional contributions from malate dehydrogenase 1 and 2 (MDH1/2). Structural modeling of the active site of LDHA demonstrates the spatial constraints for substrate binding that dictate how LDHA-mediated reduction of α-KG gives rise to L-2HG. Moreover, the present disclosure shows that L-2HG enhances trimethylation of histone 3 lysine 9 (H3K9me3) that occurs in response to hypoxia. Thus, the present disclosure demonstrates that hypoxia-induced L-2HG represents a metabolic signaling intermediate that conveys information about the metabolic state of the cell via modulation of epigenetic marks in the nucleus.

REFERENCES

Achouri, Y., Noel, G., Vertommen, D., Rider, M. H., Veiga-Da-Cunha, M., and Van Schaftingen, E. (2004). Identification of a dehydrogenase acting on D-2-hydroxyglutarate. The Biochemical Journal 381, 35-42.

Albers, E., Gustafsson, L., Niklasson, C., and Liden, G. (1998). Distribution of 14C-labelled carbon from glucose and glutamate during anaerobic growth of Saccharomyces cerevisiae. Microbiology 144 (Pt 6), 1683-1690.

Amary, M. F., Bacsi, K., Maggiani, F., Damato, S., Halai, D., Berisha, F., Pollock, R., O'Donnell, P., Grigoriadis, A., Diss, T., et al. (2011). IDH1 and IDH2 mutations are frequent events in central chondrosarcoma and central and periosteal chondromas but not in other mesenchymal tumours. The Journal of Pathology 224, 334-343.

Banks, J. L., Beard, H. S., Cao, Y., Cho, A. E., Damm, W., Farid, R., Felts, A. K., Halgren, T. A., Mainz, D. T., Maple, J. R., et al. (2005). Integrated Modeling Program, Applied Chemical Theory (IMPACT). Journal of Computational Chemistry 26, 1752-1780.

Bensaad, K., and Harris, A. L. (2014). Hypoxia and metabolism in cancer. Advances in Experimental Medicine and Biology 772, 1-39.

Borger, D. R., Tanabe, K. K., Fan, K. C., Lopez, H. U., Fantin, V. R., Straley, K. S., Schenkein, D. P., Hezel, A. F., Ancukiewicz, M., Liebman, H. M., et al. (2012). Frequent mutation of isocitrate dehydrogenase (IDH)1 and IDH2 in cholangiocarcinoma identified through broad-based tumor genotyping. The Oncologist 17, 72-79.

Cairns, R. A., Iqbal, J., Lemonnier, F., Kucuk, C., de Leval, L., Jais, J. P., Parrens, M., Martin, A., Xerri, L., Brousset, P., et al. (2012). IDH2 mutations are frequent in angioimmunoblastic T-cell lymphoma. Blood 119, 1901-1903.

Chen, C., Liu, Y., Lu, C., Cross, J. R., Morris, J. P.t., Shroff, A. S., Ward, P. S., Bradner, J. E., Thompson, C., and Lowe, S. W. (2013). Cancer-associated IDH2 mutants drive an acute myeloid leukemia that is susceptible to Brd4 inhibition. Genes & Development 27, 1974-1985.

Chowdhury, R., Yeoh, K. K., Tian, Y. M., Hillringhaus, L., Bagg, E. A., Rose, N. R., Leung, L K., Li, X. S., Woon, E. C., Yang, M., et al. (2011). The oncometabolite 2-hydroxyglutarate inhibits histone lysine demethylases. EMBO Reports 12, 463-469.

Dang, L., White, D. W., Gross, S., Bennett, B. D., Bittinger, M. A., Driggers, E. M., Fantin, V. R., Jang, H. G., Jin, S., Keenan, M. C., et al. (2009). Cancer-associated IDH1 mutations produce 2-hydroxyglutarate. Nature 462, 739-744.

DeBerardinis, R. J., Mancuso, A., Daikhin, E., Nissim, I., Yudkoff, M., Wehrli, S., and Thompson, C. B. (2007). Beyond aerobic glycolysis: transformed cells can engage in glutamine metabolism that exceeds the requirement for protein and nucleotide synthesis. Proceedings of the National Academy of Sciences of the United States of America 104, 19345-19350.

Figueroa, M. E., Abdel-Wahab, O., Lu, C., Ward, P. S., Patel, J., Shih, A., Li, Y., Bhagwat, N., Vasanthakumar, A., Fernandez, H. F., et al. (2010). Leukemic IDH1 and IDH2 mutations result in a hypermethylation phenotype, disrupt TET2 function, and impair hematopoietic differentiation. Cancer Cell 18, 553-567.

Friesner, R. A., Banks, J. L., Murphy, R. B., Halgren, T. A., Klicic, J. J., Mainz, D. T., Repasky, M. P., Knoll, E. H., Shelley, M., Perry, J. K., et al. (2004). Glide: a new approach for rapid, accurate docking and scoring. 1. Method and assessment of docking accuracy. Journal of Medicinal Chemistry 47, 1739-1749.

Friesner, R. A., Murphy, R. B., Repasky, M. P., Frye, L. L., Greenwood, J. R., Halgren, T. A., Sanschagrin, P. C., and Mainz, D. T. (2006). Extra precision glide: docking and scoring incorporating a model of hydrophobic enclosure for protein-ligand complexes. Journal of Medicinal Chemistry 49, 6177-6196.

Gross, S., Cairns, R. A., Minden, M. D., Driggers, E. M., Bittinger, M. A., Jang, H. G., Sasaki, M., Jin, S., Schenkein, D. P., Su, S. M., et al. (2010). Cancer-associated metabolite 2-hydroxyglutarate accumulates in acute myelogenous leukemia with isocitrate dehydrogenase 1 and 2 mutations. The Journal of Experimental Medicine 207, 339-344.

Halgren, T. A., Murphy, R. B., Friesner, R. A., Beard, H. S., Frye, L. L., Pollard, W. T., and Banks, J. L. (2004). Glide: a new approach for rapid, accurate docking and scoring. 2. Enrichment factors in database screening. Journal of Medicinal Chemistry 47, 1750-1759.

Haliloglu, G., Jobard, F., Oguz, K. K., Anlar, B., Akalan, N., Coskun, T., Sass, J. O., Fischer, J., and Topcu, M. (2008). L-2-hydroxyglutaric aciduria and brain tumors in children with mutations in the L2HGDH gene: neuroimaging findings. Neuropediatrics 39, 119-122.

Hu, C. J., Wang, L. Y., Chodosh, L. A., Keith, B., and Simon, M. C. (2003). Differential roles of hypoxia-inducible factor 1alpha (HIF-1alpha) and HIF-2alpha in hypoxic gene regulation. Molecular and Cellular Biology 23, 9361-9374.

Jacobson, M. P., Friesner, R. A., Xiang, Z., and Honig, B. (2002). On the role of the crystal environment in determining protein side-chain conformations. Journal of Molecular Biology 320, 597-608.

Jacobson, M. P., Pincus, D. L., Rapp, C. S., Day, T. J., Honig, B., Shaw, D. E., and Friesner, R. A. (2004). A hierarchical approach to all-atom protein loop prediction. Proteins 55, 351-367.

Kaelin, W. G., Jr., and McKnight, S. L. (2013). Influence of metabolism on epigenetics and disease. Cell 153, 56-69.

Kaelin, W. G., Jr., and Ratcliffe, P. J. (2008). Oxygen sensing by metazoans: the central role of the HIF hydroxylase pathway. Molecular Cell 30, 393-402.

Kats, L. M., Reschke, M., Taulli, R., Pozdnyakova, O., Burgess, K., Bhargava, P., Straley, K., Karnik, R., Meissner, A., Small, D., et al. (2014). Proto-oncogenic role of mutant IDH2 in leukemia initiation and maintenance. Cell Stem Cell 14, 329-341.

Koivunen, P., Lee, S., Duncan, C. G., Lopez, G., Lu, G., Ramkissoon, S., Losman, J. A., Joensuu, P., Bergmann, U., Gross, S., et al. (2012). Transformation by the (R)-enantiomer of 2-hydroxyglutarate linked to EGLN activation. Nature 483, 484-488.

Kooistra, S. M., and Helin, K. (2012). Molecular mechanisms and potential functions of histone demethylases. Nature Reviews Molecular Cell Biology 13, 297-311.

Kranendijk, M., Struys, E. A., Salomons, G. S., Van der Knaap, M. S., and Jakobs, C. (2012). Progress in understanding 2-hydroxyglutaric acidurias. Journal of Inherited Metabolic Disease.

Ley, T. J., Mardis, E. R., Ding, L., Fulton, B., McLellan, M. D., Chen, K., Dooling, D., Dunford-Shore, B. H., McGrath, S., Hickenbotham, M., et al. (2008). DNA sequencing of a cytogenetically normal acute myeloid leukaemia genome. Nature 456, 66-72.

Linster, C. L., Van Schaftingen, E., and Hanson, A. D. (2013). Metabolite damage and its repair or pre-emption. Nature Chemical Biology 9, 72-80.

Losman, J. A., and Kaelin, W. G., Jr. (2013). What a difference a hydroxyl makes: mutant IDH, (R)-2-hydroxyglutarate, and cancer. Genes & Development 27, 836-852.

Losman, J. A., Looper, R. E., Koivunen, P., Lee, S., Schneider, R. K., McMahon, C., Cowley, G. S., Root, D. E., Ebert, B. L., and Kaelin, W. G., Jr. (2013). (R)-2-hydroxyglutarate is sufficient to promote leukemogenesis and its effects are reversible. Science 339, 1621-1625.

Lu, C., Ward, P. S., Kapoor, G. S., Rohle, D., Turcan, S., Abdel-Wahab, O., Edwards, C. R., Khanin, R., Figueroa, M. E., Melnick, A., et al. (2012). IDH mutation impairs histone demethylation and results in a block to cell differentiation. Nature 483, 474-478.

Meister, A. (1950). Reduction of alpha gamma-diketo and alpha-keto acids catalyzed by muscle preparations and by crystalline lactic dehydrogenase. The Journal of Biological Chemistry 184, 117-129.

Metallo, C. M., Gameiro, P. A., Bell, E. L., Mattaini, K. R., Yang, J., Hiller, K., Jewell, C. M., Johnson, Z. R., Irvine, D. J., Guarente, L., et al. (2012). Reductive glutamine metabolism by IDH1 mediates lipogenesis under hypoxia. Nature 481, 380-384.

Millard, P., Letisse, F., Sokol, S., and Portais, J. C. (2012). IsoCor: correcting MS data in isotope labeling experiments. Bioinformatics 28, 1294-1296.

Moroni, I., Bugiani, M., D'Incerti, L., Maccagnano, C., Rimoldi, M., Bissola, L., Pollo, B., Finocchiaro, G., and Uziel, G. (2004). L-2-hydroxyglutaric aciduria and brain malignant tumors: a predisposing condition? Neurology 62, 1882-1884.

Nombela-Arrieta, C., Pivarnik, G., Winkel, B., Canty, K. J., Harley, B., Mahoney, J. E., Park, S. Y., Lu, J., Protopopov, A., and Silberstein, L. E. (2013). Quantitative imaging of haematopoietic stem and progenitor cell localization and hypoxic status in the bone marrow microenvironment. Nature Cell Biology 15, 533-543.

Olsson, M. H. M., Sondergaard, C. R., Rostkowski, M., and Jensen, J. H. (2011). PROPKA3: Consistent Treatment of Internal and Surface Residues in Empirical pK(a) Predictions. J Chem Theory Comput 7, 525-537.

Ozer, A., and Bruick, R. K. (2007). Non-heme dioxygenases: cellular sensors and regulators jelly rolled into one? Nature Chemical Biology 3, 144-153.

Parsons, D. W., Jones, S., Zhang, X., Lin, J. C., Leary, R. J., Angenendt, P., Mankoo, P., Carter, H., Siu, I. M., Gallia, G. L., et al. (2008). An integrated genomic analysis of human glioblastoma multiforme. Science 321, 1807-1812.

Patel, J. P., Gonen, M., Figueroa, M. E., Fernandez, H., Sun, Z., Racevskis, J., Van Vlierberghe, P., Dolgalev, I., Thomas, S., Aminova, O., et al. (2012). Prognostic relevance of integrated genetic profiling in acute myeloid leukemia. The New England Journal of Medicine 366, 1079-1089.

Patterson, A. L., Vanderhelm, D., Johnson, C. K., and Minkin, J. A. (1962). Absolute Configuration of Naturally Occurring Isocitric Acid. J Am Chem Soc 84, 309-&.

Read, J. A., Winter, V. J., Eszes, C. M., Sessions, R. B., and Brady, R. L. (2001). Structural basis for altered activity of M- and H-isozyme forms of human lactate dehydrogenase. Proteins 43, 175-185.

Rohle, D., Popovici-Muller, J., Palaskas, N., Turcan, S., Grommes, C., Campos, C., Tsoi, J., Clark, O., Oldrini, B., Komisopoulou, E., et al. (2013). An inhibitor of mutant IDH1 delays growth and promotes differentiation of glioma cells. Science 340, 626-630.

Rzem, R., Veiga-da-Cunha, M., Noel, G., Goffette, S., Nassogne, M. C., Tabarki, B., Scholler, C., Marquardt, T., Vikkula, M., and Van Schaftingen, E. (2004). A gene encoding a putative FAD-dependent L-2-hydroxyglutarate dehydrogenase is mutated in L-2-hydroxyglutaric aciduria. Proceedings of the National Academy of Sciences of the United States of America 101, 16849-16854.

Rzem, R., Vincent, M. F., Van Schaftingen, E., and Veiga-da-Cunha, M. (2007). L-2-hydroxyglutaric aciduria, a defect of metabolite repair. Journal of Inherited Metabolic Disease 30, 681-689.

Sasaki, M., Knobbe, C. B., Munger, J. C., Lind, E. F., Brenner, D., Brustle, A., Harris, I. S., Holmes, R., Wakeham, A., Haight, J., et al. (2012). IDH1(R132H) mutation increases murine haematopoietic progenitors and alters epigenetics. Nature 488, 656-659.

Schatz, L., and Segal, H. L. (1969). Reduction of alpha-ketoglutarate by homogeneous lactic dehydrogenase X of testicular tissue. The Journal of biological chemistry 244, 4393-4397.

Schrödinger (2014). Schrödinger Release 2014-3: Maestro, version 9.9, Schrödinger, LLC, New York, N.Y.

Semenza, G. L. (2013). HIF-1 mediates metabolic responses to intratumoral hypoxia and oncogenic mutations. The Journal of Clinical Investigation 123, 3664-3671.

Shim, E. H., Livi, C. B., Rakheja, D., Tan, J., Benson, D., Parekh, V., Kho, E. Y., Ghosh, A. P., Kirkman, R., Velu, S., et al. (2014). 1-2-Hydroxyglutarate: An Epigenetic Modifier and Putative Oncometabolite in Renal Cancer. Cancer Discovery 4, 1290-1298.

Simon, M. C., and Keith, B. (2008). The role of oxygen availability in embryonic development and stem cell function. Nature Reviews Molecular Cell Biology 9, 285-296.

Sondergaard, C. R., Olsson, M. H. M., Rostkowski, M., and Jensen, J. H. (2011). Improved Treatment of Ligands and Coupling Effects in Empirical Calculation and Rationalization of pK(a) Values. J Chem Theory Comput 7, 2284-2295.

Spencer, J. A., Ferraro, F., Roussakis, E., Klein, A., Wu, J., Runnels, J. M., Zaher, W., Mortensen, L. J., Alt, C., Turcotte, R., et al. (2014). Direct measurement of local oxygen concentration in the bone marrow of live animals. Nature 508, 269-273.

Sprecher, M., Berger, R., and Sprinson, D. B. (1964). Stereochemical Course of the Isocitrate Lyase Reaction. The Journal of Biological Chemistry 239, 4268-4271.

Struys, E. A., Gibson, K. M., and Jakobs, C. (2007). Novel insights into L-2-hydroxyglutaric aciduria: mass isotopomer studies reveal 2-oxoglutaric acid as the metabolic precursor of L-2-hydroxyglutaric acid. Journal of Inherited Metabolic Disease 30, 690-693.

Struys, E. A., Salomons, G. S., Achouri, Y., Van Schaftingen, E., Grosso, S., Craigen, W. J., Verhoeven, N. M., and Jakobs, C. (2005). Mutations in the D-2-hydroxyglutarate dehydrogenase gene cause D-2-hydroxyglutaric aciduria. American Journal of Human Genetics 76, 358-360.

Suda, T., Takubo, K., and Semenza, G. L. (2011). Metabolic regulation of hematopoietic stem cells in the hypoxic niche. Cell Stem Cell 9, 298-310.

Tausendschon, M., Dehne, N., and Brune, B. (2011). Hypoxia causes epigenetic gene regulation in macrophages by attenuating Jumonji histone demethylase activity. Cytokine 53, 256-262.

Terunuma, A., Putluri, N., Mishra, P., Mathe, E. A., Dorsey, T. H., Yi, M., Wallace, T. A., Issaq, H. J., Zhou, M., Killian, J. K., et al. (2014). MYC-driven accumulation of 2-hydroxyglutarate is associated with breast cancer prognosis. The Journal of Clinical Investigation 124, 398-412.

Vander Heiden, M. G., Cantley, L. C., and Thompson, C. B. (2009). Understanding the Warburg effect: the metabolic requirements of cell proliferation. Science 324, 1029-1033.

Venneti, S., Felicella, M. M., Coyne, T., Phillips, J. J., Gorovets, D., Huse, J. T., Kofler, J., Lu, C., Tihan, T., Sullivan, L. M., et al. (2013a). Histone 3 lysine 9 trimethylation is differentially associated with isocitrate dehydrogenase mutations in oligodendrogliomas and high-grade astrocytomas. Journal of Neuropathology and Experimental Neurology 72, 298-306.

Venneti, S., Garimella, M. T., Sullivan, L. M., Martinez, D., Huse, J. T., Heguy, A., Santi, M., Thompson, C. B., and Judkins, A. R. (2013b). Evaluation of histone 3 lysine 27 trimethylation (H3K27me3) and enhancer of Zest 2 (EZH2) in pediatric glial and glioneuronal tumors shows decreased H3K27me3 in H3F3A K27M mutant glioblastomas. Brain Pathol 23, 558-564.

Wang, F., Travins, J., DeLaBarre, B., Penard-Lacronique, V., Schalm, S., Hansen, E., Straley, K., Kernytsky, A., Liu, W., Gliser, C., et al. (2013). Targeted inhibition of mutant IDH2 in leukemia cells induces cellular differentiation. Science 340, 622-626.

Wang, Y. H., Israelsen, W. J., Lee, D., Yu, V. W., Jeanson, N. T., Clish, C. B., Cantley, L. C., Vander Heiden, M. G., and Scadden, D. T. (2014). Cell-state-specific metabolic dependency in hematopoiesis and leukemogenesis. Cell 158, 1309-1323.

Ward, P. S., Cross, J. R., Lu, C., Weigert, O., Abel-Wahab, O., Levine, R. L., Weinstock, D. M., Sharp, K. A., and Thompson, C. B. (2012). Identification of additional IDH mutations associated with oncometabolite R(-)-2-hydroxyglutarate production. Oncogene 31, 2491-2498.

Ward, P. S., Patel, J., Wise, D. R., Abdel-Wahab, O., Bennett, B. D., Coller, H. A., Cross, J. R., Fantin, V. R., Hedvat, C. V., Perl, A. E., et al. (2010). The common feature of leukemia-associated IDH1 and IDH2 mutations is a neomorphic enzyme activity converting alpha-ketoglutarate to 2-hydroxyglutarate. Cancer Cell 17, 225-234.

Ward, P. S., and Thompson, C. B. (2012). Metabolic reprogramming: a cancer hallmark even warburg did not anticipate. Cancer Cell 21, 297-308.

Wise, D. R., DeBerardinis, R. J., Mancuso, A., Sayed, N., Zhang, X. Y., Pfeiffer, H. K., Nissim, I., Daikhin, E., Yudkoff, M., McMahon, S. B., et al. (2008). Myc regulates a transcriptional program that stimulates mitochondrial glutaminolysis and leads to glutamine addiction. Proceedings of the National Academy of Sciences of the United States of America 105, 18782-18787.

Wise, D. R., and Thompson, C. B. (2010). Glutamine addiction: a new therapeutic target in cancer. Trends in Biochemical Sciences 35, 427-433.

Wise, D. R., Ward, P. S., Shay, J. E., Cross, J. R., Gruber, J. J., Sachdeva, U. M., Platt, J. M., DeMatteo, R. G., Simon, M. C., and Thompson, C. B. (2011). Hypoxia promotes isocitrate dehydrogenase-dependent carboxylation of alpha-ketoglutarate to citrate to support cell growth and viability. Proceedings of the National Academy of Sciences of the United States of America 108, 19611-19616.

Xie, H., Hanai, J., Ren, J. G., Kats, L., Burgess, K., Bhargava, P., Signoretti, S., Billiard, J., Duffy, K. J., Grant, A., et al. (2014). Targeting lactate dehydrogenase—a inhibits tumorigenesis and tumor progression in mouse models of lung cancer and impacts tumor-initiating cells. Cell Metabolism 19, 795-809.

Xu, W., Yang, H., Liu, Y., Yang, Y., Wang, P., Kim, S. H., Ito, S., Yang, C., Xiao, M. T., Liu, L. X., et al. (2011). Oncometabolite 2-hydroxyglutarate is a competitive inhibitor of alpha-ketoglutarate-dependent dioxygenases. Cancer Cell 19, 17-30.

Yan, H., Parsons, D. W., Jin, G., McLendon, R., Rasheed, B. A., Yuan, W., Kos, I., Batinic-Haberle, I., Jones, S., Riggins, G. J., et al. (2009). IDH1 and IDH2 mutations in gliomas. The New England Journal of Medicine 360, 765-773.

Zhdanov, A. V., Waters, A. H., Golubeva, A. V., and Papkovsky, D. B. (2014). Differential contribution of certain metabolic substrates and cellular oxygen in HIF signalling. Experimental Cell Research.

What is claimed is:

1. A method of treating tissue hypoxia or hypoxia-induced injury in a subject, the method comprising:
administering a therapy directed to tissue hypoxia or to hypoxia-induced injury to a subject having hypoxia or hypoxia-induced injury, wherein the subject has been determined to have a level of L-2-hydroxyglutarate ((S)-2-hydroxyglutarate or "L-2HG") that is elevated at least two-fold compared to a reference level correlated with normoxia due to the hypoxia or hypoxia-induced injury.

2. The method of claim 1, wherein the therapy comprises a therapy selected from supplemental oxygen therapy, transfusion of packed red blood cells, caffeine, vitamin therapy, mechanical ventilation, positive pressure therapy, physical exercise, and surgical intervention.

3. The method of claim 1, wherein the hypoxia-induced injury is ischemic tissue injury and wherein the therapy comprises administering an agent that modulates level of L-2HG.

4. The method of claim 1, wherein the level of L-2HG is determined by gas chromatography-mass spectrometry, liquid chromatography-mass spectrometry or enzymatic assay.

5. The method of claim 3, wherein the agent that modulates the level of L-2HG is selected from the group consisting of alpha-ketoglutarate, glutamine, and glutamate.

6. The method of claim 5, wherein the alpha-ketoglutarate is a cell-permeable variant of alpha-ketoglutarate.

7. The method of claim 6, wherein the cell-permeable variant of alpha-ketoglutarate is dimethyl alpha-ketoglutarate.

8. The method of claim 1, wherein the level of L-2HG is elevated at least three-fold, at least four-fold, at least five-fold, at least six-fold, at least seven-fold, at least eight-fold, at least nine-fold, or at least ten-fold compared to the reference level.

9. The method of claim 1, wherein the level of L-2HG is measured in a sample selected from blood, urine, serum, lymph, and cerebrospinal fluid.

* * * * *

SEQUENCE LISTING

<160> NUMBER OF SEQ ID NOS: 20

<210> SEQ ID NO 1
<211> LENGTH: 58
<212> TYPE: DNA
<213> ORGANISM: Artificial Sequence
<220> FEATURE:
<223> OTHER INFORMATION: shRNA

<400> SEQUENCE: 1
ccggccacag atgttatgga tataactcga gttatatcca taacatctgt ggttttg    58

<210> SEQ ID NO 2
<211> LENGTH: 58
<212> TYPE: DNA
<213> ORGANISM: Artificial Sequence
<220> FEATURE:
<223> OTHER INFORMATION: shRNA

<400> SEQUENCE: 2
ccggcgcatt cttcatgtga gaaatctcga gatttctcac atgaagaatg cgttttg    58

<210> SEQ ID NO 3
<211> LENGTH: 58
<212> TYPE: DNA
<213> ORGANISM: Artificial Sequence
<220> FEATURE:
<223> OTHER INFORMATION: shRNA

<400> SEQUENCE: 3
ccgggcaaca gtgaagtatc ttcaactcga gttgaagata cttcactgtt gcttttg    58

<210> SEQ ID NO 4
<211> LENGTH: 58
<212> TYPE: DNA
<213> ORGANISM: Artificial Sequence
<220> FEATURE:
<223> OTHER INFORMATION: shRNA

<400> SEQUENCE: 4
ccgggctttg tcatttgccc aggatctcga gatcctgggc aaatgacaaa gcttttg    58

<210> SEQ ID NO 5
<211> LENGTH: 58
<212> TYPE: DNA
<213> ORGANISM: Artificial Sequence
<220> FEATURE:
<223> OTHER INFORMATION: shRNA

<400> SEQUENCE: 5
ccgggcgtgt ctggaattct ggtttctcga gaaaccagaa ttccagacac gcttttg    58

<210> SEQ ID NO 6
<211> LENGTH: 58
<212> TYPE: DNA
<213> ORGANISM: Artificial Sequence
<220> FEATURE:
<223> OTHER INFORMATION: shRNA

<400> SEQUENCE: 6
ccggcgacca gaggaaagtc aagatctcga gatcttgact ttcctctggt cgttttg    58

<210> SEQ ID NO 7
<211> LENGTH: 58
<212> TYPE: DNA
<213> ORGANISM: Artificial Sequence
<220> FEATURE:
<223> OTHER INFORMATION: shRNA

<400> SEQUENCE: 7
ccgggccgtt ctccacggtg tctaactcga gttagacacc gtggagaacg gcttttg    58

<210> SEQ ID NO 8
<211> LENGTH: 58
<212> TYPE: DNA
<213> ORGANISM: Artificial Sequence

```
<220> FEATURE:
<223> OTHER INFORMATION: shRNA

<400> SEQUENCE: 8
ccggcctgtc tgcattcgag ttcatctcga gatgaactcg aatgcagaca ggttttg      58

<210> SEQ ID NO 9
<211> LENGTH: 19
<212> TYPE: RNA
<213> ORGANISM: Homo sapiens

<400> SEQUENCE: 9
gcauaauguu ggcgucaaa                                                19

<210> SEQ ID NO 10
<211> LENGTH: 19
<212> TYPE: RNA
<213> ORGANISM: Homo sapiens

<400> SEQUENCE: 10
gcuugugagu ggaugggua                                                19

<210> SEQ ID NO 11
<211> LENGTH: 19
<212> TYPE: RNA
<213> ORGANISM: Homo sapiens

<400> SEQUENCE: 11
gcaagaacua ugacggaga                                                19

<210> SEQ ID NO 12
<211> LENGTH: 19
<212> TYPE: RNA
<213> ORGANISM: Homo sapiens

<400> SEQUENCE: 12
gcgccacuau gccgacaaa                                                19

<210> SEQ ID NO 13
<211> LENGTH: 19
<212> TYPE: RNA
<213> ORGANISM: Homo sapiens

<400> SEQUENCE: 13
gggagaauuu gucacgacu                                                19

<210> SEQ ID NO 14
<211> LENGTH: 19
<212> TYPE: RNA
<213> ORGANISM: Homo sapiens

<400> SEQUENCE: 14
agguuauugu ugugggu aa                                               19

<210> SEQ ID NO 15
<211> LENGTH: 19
<212> TYPE: RNA
<213> ORGANISM: Homo sapiens

<400> SEQUENCE: 15
gaucugagcc acaucgaga                                                19

<210> SEQ ID NO 16
```

```
<211> LENGTH: 19
<212> TYPE: RNA
<213> ORGANISM: Homo sapiens

<400> SEQUENCE: 16
cgccugaccc ucuaugaua                                                        19

<210> SEQ ID NO 17
<211> LENGTH: 19
<212> TYPE: RNA
<213> ORGANISM: Homo sapiens

<400> SEQUENCE: 17
ggagaaagcc gucuuaauu                                                        19

<210> SEQ ID NO 18
<211> LENGTH: 19
<212> TYPE: RNA
<213> ORGANISM: Homo sapiens

<400> SEQUENCE: 18
ggcaaagacu auaauguaa                                                        19

<210> SEQ ID NO 19
<211> LENGTH: 19
<212> TYPE: RNA
<213> ORGANISM: Homo sapiens

<400> SEQUENCE: 19
uaagggucuu uacggaaua                                                        19

<210> SEQ ID NO 20
<211> LENGTH: 19
<212> TYPE: RNA
<213> ORGANISM: Homo sapiens

<400> SEQUENCE: 20
aaagucuucu gaugucaua                                                        19
```